United States Patent [19]
Yamashita et al.

[11] Patent Number: 4,737,519
[45] Date of Patent: Apr. 12, 1988

[54] SUBSTITUTED NAPHTHALENES, INDOLES, BENZOFURANS, AND BENZOTHIOPHENES AS LIPOXYGENASE INHIBITORS

[75] Inventors: Ayako Yamashita; Herbert G. Johnson, both of Kalamazoo, Mich.

[73] Assignee: The Upjohn Company, Kalamazoo, Mich.

[21] Appl. No.: 878,115

[22] Filed: Jun. 25, 1986

Related U.S. Application Data

[63] Continuation-in-part of Ser. No. 561,601, Dec. 14, 1983, abandoned, and Ser. No. 668,111, Nov. 5, 1984, abandoned.

[51] Int. Cl.$^4$ .................. C07C 69/94; C07C 101/04; C07D 209/08; C07D 333/52; C07D 307/86
[52] U.S. Cl. .................. 514/510; 514/415; 514/443; 514/469; 514/822; 514/826; 514/851; 514/853; 514/854; 514/855; 514/906; 548/516; 549/51; 549/469; 560/22; 560/43; 560/139; 560/173
[58] Field of Search .................. 560/139, 173, 22, 43; 514/822, 826, 851, 853, 854, 855, 906, 415, 443, 469, 510; 548/516; 549/51, 469

[56] References Cited

U.S. PATENT DOCUMENTS

| | | | |
|---|---|---|---|
| 2,917,502 | 12/1959 | Schwyzer et al. | 560/139 |
| 3,948,958 | 4/1976 | Rapoport et al. | 260/396 |
| 4,035,512 | 7/1977 | Sugihara et al. | 560/139 |
| 4,199,531 | 4/1980 | Terao et al. | 260/607 |
| 4,320,065 | 3/1982 | Dotz | 260/438 |
| 4,358,461 | 11/1982 | Maki et al. | 424/331 |
| 4,374,775 | 2/1983 | Dotz | 260/396 |
| 4,388,312 | 6/1983 | Terao et al. | 424/244 |
| 4,393,075 | 7/1983 | Terao et al. | 242/304 |
| 4,617,407 | 10/1986 | Young et la. | 549/469 |

FOREIGN PATENT DOCUMENTS

| | | |
|---|---|---|
| 0146243 | 6/1985 | European Pat. Off. |
| 2802666 | 1/1978 | Fed. Rep. of Germany |
| 45-10339 | 4/1970 | Japan |
| 1122085 | 7/1968 | United Kingdom |

OTHER PUBLICATIONS

W. D. Wulff et al., Abstracts 88 and 89, American Chemical Society Meeting, Washington, D.C. (Aug. 18–19, 1983).
K. H. Dotz et al., XXIV Synthese von Naphthol–Derivaten Aus Carbonyl–Carben–Komplexen und Alkinen: Regioselektiver Einbau Des Alkins in Das Naphthalin–Gerust, J. of Organometal. Chem., 247:187–201 (1983).
K. Buggle et al., Decomposition Products of Pyrazolines Formed from 3-Alkylthioinden-1-Ones and Diazomethane, J. Chem. Soc. Perkin Trans., I, 572–575 (1975).
K. H. Dotz, IX Carbenliganden, Carbonylliganden und Alkine Als Bausteine fur Isocyclische und Heterocyclische Systeme, J. Organomet. Chem., 140(2):177–186 (1977).
K. H. Dotz et al., Templat-Reaktionen an Chrom(O): Stereoselektive Synthese Komplexgebundener Substituierter Naphthaline, Chem. Ber., 110:1555–1563 (1977).
C. D. Snyder et al., Synthesis of Menaquinone, J. Am. Chem. Soc., 96(26):8046–8054 (1974).
F. M. Dean et al., Spirans, Part 11, A New Method for Generating O-Quinone Methides, and Its Applications to the Synthesis of Spirochromans, J. Chem. Soc., Perkin Trans. I, 2289–2294 (1977).
O. Goncalves de Lima et al., Atividade Antimicrobiana Dos Compostos Intermediarios E Do Produto de Sintese 7-Metoxi-3,9-Dimetil-1-Oxafenaleno, Rev. Inst. Antibiot., Univ. Recife, 5N(½):3–9 (1963).
K. H. Dotz et al., Templat-Reaktionen an Chrom(O): Stereoselektive Synthese Kondensierter Aromatischer Liganden aus Pentacarbonyl-Carben-Chrom-Komplexen und Alkinen, Chem. Ber., 111:2517–2526 (1978).
J. G. Widdicombe, Control of Secretion of Tracheobronchial Mucus, Brit. Med. Bull., 34:57–61 (1978).
Z. Marom et al., Slow-Reacting Substances, Leukotrienes $C_4$ and $D_{45}$ Increase the Release of Mucus from Human Airways in vitro, Am. Rev. Respir. Dis., 126:449–451 (1982).
S. J. Coles etal., Effects of Leukotrienes $C_4$ and $D_4$ on Glycoprotein and Lysozyme Secretion by Human Bronchial Mucosa, Prostaglandins, 25(No. 2):155–170 (1983).
H. G. Johnson et al., Leukotriene-$C_4$ Enhances Mucus Production from Submucosal Glands in Canine Trachea in Vivo, Int. J. Immunopharmacol., 5(No. 5):391–396 (1983).
H. G. Johnson et al., Secretogogue Responses of Leukotriene $C_4$, $D_4$: Comparison of Potency in Canine Trachea in Vivo, Prostaglandins, 25(No. 2):237–243 (1983).

(List continued on next page.)

*Primary Examiner*—Veronica P. Hoke
*Attorney, Agent, or Firm*—Martha A. Cox

[57] ABSTRACT

The present invention provides certain novel substituted naphthalenes, indoles, benzofurans, and benzothiophenes of Formula I which are useful as inhibitors of leukotriene biosynthesis and as inhibitors of lipoxygenase. They are thus employed wherever it is medically necessary or desirable to inhibit these systems.

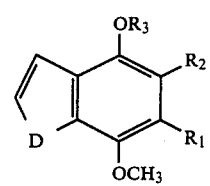

25 Claims, No Drawings

OTHER PUBLICATIONS

Z. Marom et al., Effects of Arachidonic Acid, Monohydroxyeicosatetraenoic Acid and Prostaglandins on the Release of Mucous Glycoproteins from Human Airways in Vitro, J. Clin. Invest., 67:1695–1702 (1981).

A. C. Peatfield et al., The Effect of Leukotriene $C_4$ on Mucin Release into the Cat Trachea in vivo and in vitro, Br. J. Pharmac., 77:391–393 (1982).

J. H. Shelhamer et al., The Effects of Arachinoids and Leukotrienes on the Release of Mucus from Human Airways, Chest 81:36S–37S (1982).

O. Cromwell et al., Identification of Leukotrienes D and B in Sputum from Cystic Fibrosis Patients, The Lancet, Jul. 25, 1981, pp. 164–165.

T. Ahmed et al. Abnormal Mucociliary Transport in Allergic Patients with Antigen-Induced Bronchospasm: Role of Slow Reacting Substance of Anaphylaxis, Am. Rev. Respir. Dis., 124:110–114 (1981).

M. Hamberg et al., Prostaglandin Endoperoxides, Novel Transformations of Arachidonic Acid in Human Platelets, Proc. Nat. Acad. Sci., USA, 71(No. 9):3400–3404, Sep. 1974.

M. Shiraishi et al., Studies on the Synthesis of 5-Lipoxygenase Inhibitors, J. Pharm. Dyn., 7(No. 5): s-95 (1984).

M. Shiraishi and S. Terao, Quinones, Part 3, Synthesis of Quinone Derivatives Having Ethylenic and Acetylenic Bonds: Specific Inhibitors of the Formation of Leukotrienes and 5-Hydroxyicosa-6,8,11,14-Tetraenoic Acid (5-HETE), J. Chem. Soc. Perkin Trans. I, 1591–1599 (1983).

SUBSTITUTED NAPHTHALENES, INDOLES, BENZOFURANS, AND BENZOTHIOPHENES AS LIPOXYGENASE INHIBITORS

CROSS-REFERENCE TO RELATED APPLICATION

This application is a continuation-in-part of copending application Ser. No. 561,601, filed Dec. 14, 1983; and Ser. No. 668,111, filed Nov. 5, 1984, all now abandoned.

BACKGROUND OF THE INVENTION

The present invention provides novel compositions of matter. In particular, the present invention provides novel substituted naphthalenes, indoles, benzofurans, and benzothiophenes which are useful as inhibitors of the synthesis of leukotrienes and as inhibitors of the action of lipoxygenase in mammalian metabolism.

The leukotrienes are a class of unsaturated fatty acid compounds which are derived from arachidonic acid by the action of lipoxygenase. See, e.g., Samuelsson, Trends in Pharmacological Sciences, 5: 227 (1980); and Samuelsson, et al., Annu. Rev. Biochem. 47: 997–1029 (1978). For a discussion of leukotriene nomenclature, see Samuelsson, et al., Prostaglandins, 19: 645 (1980).

The leukotrienes have been discovered as potent constrictors of human bronchi. That is, certain leukotrienes are mediators of the action of slow-reacting substance of anaphylaxis (SRS-A). See, e.g., Dahlen, Nature, 288: 484 (1980). These compounds are therefore important mediators of bronchoconstriction in humans.

The role of leukotrienes as agonists in immediate hypersensitivity and other pathological conditions has led to research into inhibitors of leukotriene biosynthesis and leukotriene antagonists. See, e.g., Corey, et al., Tet. Lett. 21: 4243 (1980).

Mucus secreted from submucosal glands and surface at the epithelial cells combines with water to form part of the respiratory tract secretions. In healthy states mucous secretions in the respiratory tract is normal being about 50 to 150 ml per day in man. The excessive production of mucus, however, is an important feature of many pulmonary diseases. For example, in chronic bronchitis the flow of mucus increases up to four times. The lack of the ability of the patient to deal with this hyper-production leads to paths of physiological conditions of the airways such as chronic bronchitis, asthma, and cystic fibrosis where there is a defect in consistency in clearance of the mucus. Therefore it is medically desirable to regulate the hypersecretion of mucus (J. G. Widdicobe, Brit. Med. Bull., 34: 57 (1978)). Historically, attempts have been made to treat the symptoms without regulation of the root cause. For example, mucolytics, acetylcysteine containing solutions, as well as iodides have been used. Also, antibiotics are used to treat infections in cystic fibrosis because no known drug can regulate the consistency of the mucus in this disease condition.

Leukotrienes, particularly leukotriene $C_4$ ($LTC_4$) and leukotriene $D_4$ ($LTD_4$) have been shown to be potent mucous secretagogues. Both $LTC_4$ and $LTD_4$ increase the release of mucus from human airways in vitro. Z. Maron, et al., Am. Rev. Respir. Dis. 126, 449–451 (1982); S. J. Coles, et al., Prostaglandins 25, 155–170 (1983) and from canine tracheas in vivo. H. G. Johnson, et al., Int. J. Immunopharmacol. 5, 178 (1983); H. G. Johnson, et al., Prostaglandins 25, 237–243 (1983). Arachidonic acid, metabolic products of arachidonic acid, monohydroxyeicosatetraenoic acid, and prostaglandins also release mucus from human airway. Z. Marom, et al., J. Clin. Invest. 67, 1695–1702 (1981). $LTC_4$ was effective in stimulating mucus release in vivo in the cat but not in vitro on cat trachea tissue. A. C. Peatfield, et al., Br. J. Pharmac. 77, 391–393 (1982). J. H. Shelhamer, et al., Chest 81, 36S (1982) summarizes the nature of evidence available suggesting that lipoxygenase products generated by the airways in vitro might be responsible for the augmented mucus release.

O. Cromwell, et al., The Lancet, July 25, 1981, pp. 164–165, identified $LTB_4$ and $LTD_4$ in the sputum of cystic fibrosis patients and speculated, therefore, that inhibitors of the lipoxygenase pathway might be capable of reversing the airway obstruction in such patients.

T. Ahmed, et al., Am. Rev. Respir. Dis. 124, 110–114 (1981) demonstrated that FPL 55712, an $LTC_4$ antagonist when given prior to antigen challenge was effective in reversing the tracheal mucus velocity in patients with a history of bronchial asthma but concluded that the clinical significance of FPL 55712 remains to be demonstrated.

In mammalian metabolism, arachidonic acid is transformed to 12-L-hydroperoxy-5,8,10,14-eicosatetraenoic acid by the action of 12-lipoxygenase. See, Hamberg, et al., Proc. Nat. Acad. Sci. 71: 3400–3404 (1974). Similarly, 5-lipoxygenase transforms arachidonic acid into 5-S-hydroperoxy-6,8,11,14-eicosatetraenoic acid. Thus, an agent which inhibits the action of lipoxygenase would be useful in treating or preventing untoward conditions associated with lipoxygenase products.

Therefore, compounds which inhibit the action of lipoxygenase are useful in the treatment of inflammatory conditions where it is desirable to prevent migration of polymorphonuclear leukocytes to the inflammatory site. They are also useful in the treatment of asthma.

PRIOR ART

Certain chromium complexes of benzofurans and benzothiophenes are disclosed in K. H. Dötz, et al., Chem. Ber. 111: 2517 (1978).

Certain naphthaquinones are disclosed as intermediates for the preparation of Vitamin K-type derivatives in U.S. Pat. Nos. 4,374,775 and 4,320,065. U.S. Pat. Nos. 4,358,461; 4,388,312; and 4,393,075 disclose certain naphthaquinones as SRS-A and lipoxygenase inhibitors. Intermediates for these latter compounds are disclosed in U.S. Pat. No. 4,199,531. W. D. Wulff, et al., have described the use of Fischer carbene complexes in the preparation of certain hydroquinone mono ethers in Abstracts 88 and 89 from the Fall 1983 American Chemical Society Meeting in Washington D.C. (Aug. 18-19, 1983).

A number of substituted 1-hydroxy, 4-methoxy naphthalenes are known. Thus K. H. Dötz, et al., J. Organometal. Chem. 247 (2): 187–201 (1983) discloses 4-methoxy-1-naphthalenols substituted in the 2 and 3 positions by phenyl, substituted phenyl, methyl, ethyl, octyl, and propyl. 4-Methoxy-2-phenyl-1-naphthalenol is disclosed in K. Buggle, et al., J. Chem. Soc., Perkin Trans 1 (6): 572–575 (1975). 4-Methoxy-2.3-diphenyl-1-naphthalenol is disclosed in K. H. Dötz, J. Organmet. Chem. 140 (2): 177–86 (1977). 4-Methoxy-2,3-dimethyl-1-naphthalenol is disclosed in K. H. Döz, et al., Chem. Ber. 110 (4): 1555–63 (1977). 2-Tert-butyl-4-methoxy-1- naphthol is disclosed in Japanese patent 7010339. U.S. Pat. No. 3,948,958 discloses 4-methoxy-3-methyl-1-naphthenol. 4-Methoxy-2-methyl-1-naphthenol is disclosed in I. D. Snyder, et al., J. Am. Chem. Soc. 96 (26): 8046–53 (1974). The 2,3-unsubstituted 4-methoxy-1-naphthenol compound is also known. See, e.g., British patent No. 1,122,085.

Certain 1-acetoxy-4-methoxy-naphthalenes are also known. Thus, 4-methoxy-1-naphthalenol, acetate is disclosed in German OLS No. 2802666. The corresponding 2,3-dimethyl compound is disclosed in F. M. Dean, et al., J. Chem. Soc., Perkin Trans. 1 (20): 2289–94 (1977). 4-Methoxy-2-phenyl-1-naphthalenol is disclosed in O. Gonclalves de Lima, et al., Rev. Inst. Antibiot., Univ. Recife 5 (1–2): 3–9 (1963).

SUMMARY OF THE INVENTION

The present invention particularly provides: a compound of the Formula I

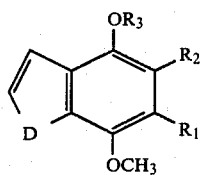

FORMULA 1 wherein $R_1$ and $R_2$ are the same or different and are
(a) hydrogen,
(b) $(C_1-C_{10})$alkyl,
(c) $(C_2-C_{10})$alkenyl, or
(d) PhX;
wherein (PhX) is phenyl substituted by zero to 3 of the following:
(a) $(C_1-C_4)$alkyl,
(b) chloro,
(c) fluoro,
(d) bromo,
(e) nitro,
(f) trifluoromethyl; or
(g) $OR_4$;
wherein D is
(a) —CH=CH—,
(b) =N(CH$_3$),
(c) —S—, or
(d) —O—;
wherein $R_3$ is
(a) $CH_3$—C(O)—,
(b) hydrogen,
—C(O)—$(CR_{17}R_{18})_m$—$(CH_2)_n$—$NR_{14}R_{15}$,
(d) —C(O)—AA, or
(e) —C(O)—PhX—NH$_2$;
wherein m is 1, 2, 3, or 4;
wherein n is 0, 1, 2, 3, 4, or 5;
wherein —C(O)AA is the acyl portion derived from any naturally occurring alpha-amino acid, to wit see page 6 of the specification;
wherein $R_{14}$ and $R_{15}$ are the same or different and are:
(a) hydrogen,
(b) $(C_1-C_{10})$alkyl,
(c) —C(O)$R_{16}$,
(d) —C(O)—PhX, or
(e) —PhX;
with the proviso that $R_{14}$ and $R_{15}$ are other than hydrogen when n is zero;
wherein $R_{16}$ is $(C_1-C_4)$alkyl;
wherein $R_{17}$ and $R_{18}$ are the same or different and are:

(a) hydrogen,
(b) $(C_1-C_{10})$alkyl,
(c) —CH$_2$—PhX, or
(d) —PhX;
with the proviso that each occurrence of $R_{17}$ and $R_{18}$ is the same or different;
wherein PhX—NH$_2$ is an amino-substituted phenyl group additionally substituted by zero to 3 of the following:
(a) $(C_1-C_4)$alkyl,
(b) chloro,
(c) fluoro,
(d) bromo,
(e) nitro,
(f) trifluoromethyl, or
(g) $OR_4$;
wherein $R_4$ is
(a) hydrogen, or
(b) $(C_1-C_4)$alkyl;
with the following provisos
(1) when D is —CH=CH— or =N(CH$_3$), $R_3$ is not hydrogen;
(2) when D is —CH=CH— and one of $R_2$ and $R_1$ is hydrogen or methyl, the other is not hydrogen or methyl;
(3) when D is =N(CH$_3$), $R_1$ and $R_2$ are not phenyl; and
(4) when D is —CH=CH— and $R_2$ is phenyl, $R_1$ is other than hydrogen
or a pharmacologically acceptable acid addition salt thereof when $R_3$ is
(c) —C(O)—$(CR_{17}R_{18})_m$—$(CH_2)_n$—$NR_{14}R_{15}$,
(d) —C(O)—AA, or
(e) —C(O)—PhX—NH$_2$.

A method for treating or preventing the hypersecretion of mucus in the respiratory tract of a patient in need thereof which comprises:

administering to said patient an amount of the compound of Formula I effective to treat or prevent said hypersecretion of mucus,
wherein $R_1$ and $R_2$ are the same or different and are
(a) hydrogen,
(b) $(C_1-C_{10})$alkyl,
(c) $(C_2-C_{10})$alkenyl, or
(d) PhX;
wherein (PhX) is phenyl substituted by zero to 3 of the following:
(a) $(C_1-C_4)$alkyl,
(b) chloro,
(c) fluoro,
(d) bromo,
(e) nitro,
(f) trifluoromethyl; or
(g) $OR_4$;
wherein D is
(a) —CH=CH—,
(b) =N(CH$_3$),
(c) —S—,
(d) —O—;
wherein $R_3$ is
(a) $CH_3$—C(O)—,
(b) hydrogen;
(c) —C(O)—$(CR_{17}R_{18})_m$—$(CH_2)_n$—$NR_{14}R_{15}$,
(d) —C(O)—AA, or
(e) —C(O)—PhX—NH$_2$;
wherein m is 1, 2, 3, or 4;
wherein n is 0, 1, 2, 3, 4, or 5;

wherein —C(O)AA is the acyl portion derived from any naturally occurring alpha-amino acid, to wit see page 6 of the specification;

wherein $R_{14}$ and $R_{15}$ are the same or different and are:
(a) hydrogen,
(b) $(C_1-C_{10})$alkyl,
(c) —C(O)$R_{16}$,
(d) —C(O)—PhX, or
(e) —PhX;

with the proviso that $R_{14}$ and $R_{15}$ are other than hydrogen when n is zero;

wherein $R_{16}$ is $(C_1-C_4)$ alkyl;

wherein $R_{17}$ and $R_{18}$ are the same or different and are:
(a) hydrogen,
(b) $(C_1-C_{10})$alkyl,
(c) —CH$_2$—PhX, or
(d) —PhX;

with the proviso that each occurrence of $R_{17}$ and $R_{18}$ may be the same or different; wherein PhX—NH$_2$ is an amino-substituted phenyl group additionally substituted by zero to 3 of the following:
(a) $(C_1-C_4)$alkyl,
(b) chloro,
(c) fluoro,
(d) bromo,
(e) nitro,
(f) trifluoromethyl, or
(g) OR$_4$;

wherein $R_4$ is
(a) hydrogen, or
(b) $(C_1-C_4)$alkyl;

with the following provisos
(1) when D is —CH=CH— or =N(CH$_3$), $R_3$ is not hydrogen;
(2) when D is —CH=CH— and one of $R_2$ and $R_1$ is hydrogen or methyl, the other is not hydrogen or methyl;
(3) when D is =N(CH$_3$), $R_1$ and $R_2$ are not phenyl; and
(4) when D is —CH=CH— and $R_2$ is phenyl, $R_1$ is other than hydrogen;

or a pharmacologically acceptable acid addition salt thereof, when $R_3$ is
(c) —C(O)—(CR$_{17}$R$_{18}$)$_m$—(CH$_2$)$_n$—NR$_{14}$R$_{15}$,
(d) —C(O)—AA, or
(e) —C(O)—PhX—NH$_2$.

The carbon atom content of various hydrocarbon-containing moieties is indicated by a prefix designating the minimum and maximum number of carbon atoms in the moiety, i.e., the prefix $(C_i-C_j)$ indicates a moiety of the integer "i" to the integer "j" carbon atoms, inclusive. Thus $(C_1-C_3)$alkyl refers to alkyl of one to 3 carbon atoms, inclusive, or methyl, ethyl, propyl, and isopropyl.

Examples of alkyl of one to 10 carbon atoms, inclusive, are methyl, ethyl, propyl, butyl, pentyl, hexyl, heptyl, octyl, nonyl, decyl, and isomeric forms thereof.

Examples of $C_2-C_{10}$ alkenyl are allyl, 1-methylallyl, 2-methylallyl (methallyl), 2-butenyl (crotyl), 3-butenyl, 1,2-dimethylallyl, 1,1-dimethylallyl, 2-ethylallyl, 1-methyl-2-butenyl, 2-methyl-2-butenyl, 3-methyl-2-butenyl, 3-pentenyl, 2,3-dimethyl-2-butenyl, 1,1,2-trimethylallyl, 1,3-dimethyl-2-butenyl, 1-ethyl-2-butenyl, 4-methyl-2-pentenyl, 2-ethyl-2-pentenyl, 4,4-dimethyl-2-pentenyl, 2-heptenyl, 2-octenyl, 5-octenyl, 1,4-dimethyl-1-hexenyl, and the like.

Examples of PhX are phenyl, p-chlorophenyl, m-bromophenyl, 2,4-difluorophenyl, 2,4,6-trichlorophenyl, p-tolyl, m-tolyl, o-tolyl, p-ethylphenyl, p-tert-butylphenyl, 2,5-dimethylphenyl, 4-chloro-2-methylphenyl, 2,4-dichloro-3-methylphenyl, p-nitrophenyl, p-methoxyphenyl, 3-trifluorophenyl, and 4-hydroxyphenyl.

Examples of acids, which are commonly used for salt formation, are hydrochloric acid, hydrobromic acid, hydroiodic acid, methanesulfonic acid, ethanesulfonic acid, benzenesulfonic acid, phosphoric acid, acetic acid, propionate acid, succinic acid, para-toluenesulfonic acid, maleic acid, tartaric acid, and lactic acid.

By —C(O)—AA is meant the acyl part of an amino acid including the naturally-occurring acids such as: glycine, alanine, valine, leucine, isoleucine, phenylalanine, lysine, proline, tryptophan, methionine, serine, threonine, cysteine, tyrosine, asparagine, glutamine, aspartic acid, glutamic acid, arginine, ornithine, and histidine, and synthetic derivatives thereof. These compounds may be in L or D configuration and are well known and readily available to those skilled in the art. Thus, AA—COOH would represent the amino acids themselves.

When $R_3$ is definitions (c), (d), or (e), the substituent is an amino acid derivative which may be in the "D" and/or "L" configuration, the prefixes "D" and "L" are a means of indicating the *relative* configurations of various optically active compounds, especially carbohydrates. The compound glyceraldehyde, CH$_2$OH-CHOHCHO, was selected as a standard of reference, because it is the simplest carbohydrate—an aldotriose—capable of optical isomerism. (+)-Glyceraldehyde was arbitrarily assigned a configuration and was designated D-glyceraldehyde, and (−)-glyceraldehyde was assigned a second configuration and was designated L-glyceraldehyde. R. T. Morrison & R. N. Boyd, *Organic Chemistry* 1087–88 (1978). Compounds related configurationally to D-glyceraldehyde are given the designation D, and compounds related to L-glyceraldehyde are given the designation L. *Organic Chemistry* at 1089. In the present invention, both L and D configurations are observed; however, the L-configuration predominates and is preferred.

The compounds of the present invention will be named herein using the Chemical Abstracts numbering system (see Naming and Indexing of Chemical Substances for Chemical Abstracts during the Ninth Collective Period (1972–1976), a reprint of section IV from the Volume 76 Index Guide.) When D is —CH=CH—, the compounds are named as naphthalenes. When D is =N(CH$_3$), the compounds are named as N-methyl indoles, and when D is —O— and —S—, the compounds are named as benzofurans and benzothiophenes, respectively.

As noted, compounds of this invention are useful to inhibit the formation of slow reacting substance—anaphylaxis (SRS-A) and thus its smooth muscle contracting and secretory effects.

To demonstrate the SRS-A inhibitory activity of the compounds of this invention, compounds of this invention were evaluated in a standard laboratory test. This test is conducted in rat mononuclear cells incubated in the presence of cysteine and challenged with a calcium ionophore (which induces SRS-A formation). Among the nonamino compounds of this invention, in this test system, 1-acetoxy-2-n-butyl-4-methoxynaphthalene (Example 3) and 1-acetoxy-2,3-diethyl-4-methoxynaphthalene (Example 4) are preferred. At a concentration of 10 micrograms/ml, these compounds inhibited the synthesis of SRS-A 100% and 95%, respectively.

Certain of the amino acyl compounds of this invention (when $R_3$ is $-C(O)-(CR_{17}R_{18})_m-(CH_2)_n-NR_{14}R_{15}$, $-C(O)-AA$ or $-C(O)-PhX-NH_2$) were evaluated in a standard laboratory test to measure the inhibition of leukotriene synthesis. Four of the amino-type compounds of this invention were preferred in this test. Specifically, in this test system, L-Valine, 2,3-diethyl-4-methoxynaphth-1-yl ester, hydrochloride; L-Valine, 2-n-butyl-4-methoxynaphth-1-yl ester; L-Valine, 2-n-butyl-4-methoxynaphth-1-yl ester, hydrochloride; and L-Alanine, 2-n-butyl-4-methoxynaphth-1-yl ester were preferred. At a concentration of 1 microgram/ml, these compounds inhibited the synthesis of leukotriene 100%, 97%, 93%, and 98%, respectively. At a concentration of 10 micrograms/ml, these compounds completely inhibited the synthesis of leukotriene.

The amino acyl compounds of this invention, when $R_3$ is $-C(O)-(CR_{17}R_{18})_m-(CH_2)_n-NR_{14}R_{15}$, $-C(O)-AA$ or $-C(O)-PhX-NH_2$, are also preferred for drug formulation because they are more easily crystallizable (particularly, the salts) and are more water soluble. On the basis of biological activity and ease of formulation, L-Valine, 2,3-diethyl-4-methoxynaphth-1-yl ester, hydrochloride is the most preferred.

The compounds of the present invention were also tested for lipoxygenase inhibition. Arachidonic acid is added to washed human platelets and the oxygen uptake is measured using oxygraph cells. A decrease of oxygen uptake versus the control cell indicates inhibition of lipoxygenase. For a full description of the procedure see, Wallach, et al., Biochim. Biophys. Acta. 231: 445 (1976).

Using this system, 1-acetoxy-2-n-butyl-4-methoxynaphthalene (Example 3) and 1-acetoxy-2,3-diethyl-4-methoxynaphthalene (Example 4) are preferred, both compounds completely inhibiting 5-HETE production at 10 μm. The former compound exhibits an $IC_{50}$ of approximately $10^{-7}M$.

Thus, some of the novel compounds of this invention have been shown to be active as inhibitors of the production of leukotrienes and some of the compounds of this invention have been shown to be active as inhibitors of the lipoxygenase enzyme system. Some of these compounds are effective in both systems. All of the compounds of this invention are active as inhibitors of at least one of these two systems. Accordingly, these novel compounds are useful for administration to mammals, including humans, whenever it is desirable medically to inhibit either of these systems. Inhibitors of either system are useful in the treatment of asthma.

Thus, all of the compounds of this invention are useful in the treatment of asthma. For example, these compounds are useful as bronchodilators or as inhibitors of mediators such as SRS-A which are released from cells activated by an antigen-antibody complex. Thus, these compounds control spasm and facilitate breathing in conditions such as bronchial asthma, bronchitis, bronchiectasis, pneumonia and emphysema. For these purposes, these compounds are administered in a variety of dosage forms, e.g., orally in the form of tablets, capsules, or liquids; rectally in the form of suppositories; parenterally, subcutaneously, or intramuscularly, with intravenous administration being preferred in emergency situations, by inhalation in the form of aerosols or solutions for nebulizers; or by insufflation in the form of powder. Doses in the range of about 0.01 to 50 mg per kg of body weight are used 1 to 4 times a day, the exact dose depending on the age, weight, and condition of the patient and on the frequency and route of administration. For the above use these compounds can be combined advantageously with other anti-asthmatic agents, such as sympathomimetics (isoproterenol, phenylephrine, ephedrine, etc.); xanthine derivatives (theophylline and aminophylline); and corticosteroids (ACTH and prednisolone).

As noted above, the compounds of this invention are particularly useful in treating asthma, but any allergy wherein slow reacting substance of anaphylaxis (SRSA) is thought to be involved as a pharmacological mediator of anaphylaxis can be treated. For example, the compounds can be used for treatment of such conditions as allergic rhinitis, food allergy and urticaria as well as asthma.

The compounds of this invention are effectively administered to human asthma patients by any covenient route such as oral inhalation, aerosol inhalation, parenterally, (orally, intravenously, interperitoneally), transdermally, topically and the like.

The amino acyl compounds of this invention are preferred for intravenous infusions and the like. Particularly preferred in this regard is L-Valine, 2-n-butyl-4-methoxy-1-naphthalenyl ester, monohydrochloride. The non-acyl-amino compounds of this invention are preferred for topical administration.

For administration by the oral inhalation route with conventional nebulizers or by oxygen aerosolization it is convenient to provide the instant active ingredient in dilute solution, preferably at concentrations of about 1 part of medicament to form about 100 to 200 parts by weight of total solution. Entirely conventional additives may be employed to stabilize these solutions or to provide isotonic media, for example, sodium chloride, sodium citrate, citric acid, sodium bissulfite, and the like can be employed.

For administration as a self-propelled dosage unit for administering the active ingredient in aerosol form suitable for inhalation therapy the composition can comprise the active ingredient suspended in an inert propellant (such as a mixture of dichlorodifluoromethane and dichlorotetrafluoroethane) together with a co-solvent, such as ethanol, flavoring materials and stabilizers. Instead of a co-solvent there can also be used a dispensing agent such as oleyl alcohol. Suitable means to employ the aerosol inhalation therapy technique are described fully in U.S. Pat. No. 2,868,691 for example.

The lipoxygenase inhibitor compounds of this invention are useful whenever it is desired to inhibit platelet aggregation, reduce the adhesive character of platelets, and remove or prevent the formation of thrombi in mammals, including man, rabbits, dogs, and rats. For example, these compounds are useful in the prevention of myocardial infarcts, to prevent post-operative thrombosis, to promote patency of vascular grafts following surgery, and to treat conditions such as atherosclerosis, arteriosclerosis, blood clotting defects due to lipemia, and other clinical conditions. For these purposes, these compounds are administered systemically, e.g., intravenously, subcutaneously, intramuscularly, and in the form of sterile implants for prolonged action. For rapid response, especially in emergency situations, the intravenous route of administration is preferred. Doses in the range about 0.005 to about 20 mg per kg of body weight per day are used, the exact dose depending on the age, weight, and condition of the patient or animal, and on the frequency and route of administration.

These lipoxygenase inhibitor compounds are further useful as additives to blood, blood products, blood substitutes, or other fluids which are used in artifical extracorporeal circulation of perfusion of isolated body portions, e.g., limbs and organs, whether attached to the original body, detached and being preserved or prepared for transplant, or attached to a new body. During these circulations and perfusions, aggregated platelets tend to block the blood vessels and portions of the circulation apparatus. This blocking is avoided by the presence of these compounds. For this purpose, the compound is added gradually or in single or multiple portions to the circulating blood, to the blood of the donor animal, to the perfused body portion, attached or detached, to the recipient, or to two or all of these at a total steady state dose of about 0.001 to 10 mg per liter of circulating fluid. It is especially useful to use these compounds in laboratory animals, e.g., cats, dogs, rabbits, monkeys, and rats, for these purposes in order to develop new methods and techniques for organ and limb transplants.

Hammerström, et al. Science 197: 994–996 (1977) notes the role of 12-lipoxygenase in psoriasis. Doig, et al., Prostaglandins 20: 1007–1019 (1980) and Lin, et al., J. Clin. Invest. 70: 1058 (1982) disclose that 5-lipoxygenase inhibitors block platlet thrombus formation. Dawson, et al., in SRS-A and Leukotrienes, 219–226 (Wiley and Sons 1981) note that 5-lipoxygenase inhibitors block neutrophil "recruitment" during inflammatory diseases such as arthritis.

In addition, 5-lipoxygenase inhibitors prevent the production of slow-reacting substance of anaphylaxis (SRS-A), now known to be a mixture of leukotrienes. (Leukotrienes are synthesized using 5-lipoxygenase.) SRS-A mediates the symptoms and pathophysiology of asthma. See Murphy, et al., Proc. Nat. Acad. Sci. USA, 4275–4279 (1979). Thus, the 5-lipoxygenase inhibitors disclosed herein are useful in the treatment of asthma.

5-Lipoxygenase products have been implicated in essential hypertension (Chand, et al., Microcirculation 1:111–123 (1981), and gout (Rae, et al., Lancet 1122–1124 (Nov. 20, 1982), indicating that the 5-lipoxygenase inhibitors disclosed herein are useful in treating these conditions as well. Further, neutrophil depletion, such as that induced by 5-lipoxygenase inhibitors, has been shown to cause a significant decrease in infarct size following circumflex artery occulsion. See Romson, et al., Circulation 66:85 (1982). Thus, the 5-lipoxygenase inhibitors herein may be useful in the protection of the myocardium following infarct.

The lipoxygenase inhibitors of the present invention are also useful for the prevention or treatment of deep vein thrombosis (DVT). This method comprises the administration of a compound of the Formula I to a mammal susceptible to DVT.

By "deep vein thrombosis" (DVT) is meant the thrombosis (clot formation) of the lower limb deep veins (deeply situated veins). Such thrombosis is frequently a result of major surgery, massive trauma, myocardial infarction, neoplasia, and pregnancy. The term "deep vein thrombosis" or "DVT" is meant to encompass the thrombosis resulting from these or any other causes.

By "prevention" in this context is meant the total or partial avoidance of clot formation in the deep veins of a mammal.

The present invention includes the treatment of each of various mammalian species, including humans. With respect to non-humans, the present invention is particularly and especially concerned with treating domesticated animals, for example, cattle, dogs, cats and swine. Humans are the most preferred mammals to be treated by the methods of this invention.

Any convenient route of administration is employed. Thus, oral formulation and oral administration is, for example, the preferred route for use in humans although parenteral (e.g., intravenous, intraperitoneal, and intramuscular) administration is also employed.

The dosage regimen for the lipoxygenase inhibitor compounds used to treat deep vein thrombosis will depend on a variety of factors, including the type, age, weight, sex, and medical condition of the mammal, and most importantly on the risks and probable consequences of deep vein thrombosis. It is within the skill of the attending physician or veterinarian to determine the risks of deep vein thrombosis, and to prescribe an effective amount of the lipoxygenase inhibitors claimed herein. When 1-acetoxy-2-butyl-4-methoxynaphthalene or 1-acetoxy2,3-diethyl-4-methoxynaphthalene are used, the dosage is in the range of about 0.01 to about 1 mg/kg/minute by intravenous infusion, or about 0.1 to about 50 mg/kg/day by oral administration. Equivalent dosages for other routes of administration are also employed. Similarly, when other lipoxygenase inhibitors are employed, equipotent doses are administered based on the compound's comparative potency as demonstrated in the standard laboratory test set forth as Example 20 below.

The most preferred use of these compounds is as SRS-A inhibitors, e.g., in the treatment of asthma.

The present invention further provides a method of treating or preventing the hypersecretion of mucus in the airways or the respiratory tract of a patient in need thereof. More particularly, the present invention provides a method for treating or preventing the hypersecretion of mucus in the respiratory tract of patients with bronchial asthma, chronic bronchitis, cystic fibrosis, bronchorrhea, obstructive bronchitis and other disease conditions associated with hyperplasia of mucus secreting cells and increased mucus secretion. The method of the present invention finds particular use in warm blooded animals including mammals, such as cattle, horses, rodents, dogs, sheep, pigs, monkeys, cats, humans, and birds. The present invention provides a prophylactic as well as therapeutic method of treating hypersecretion of mucus in the airways of a warm blooded animal.

In practicing the method of treating or preventing the hypersecretion of mucus of the present invention the quantity of compound of Formula I to be administered is any amount effective in treating or preventing hypersecretion of mucus in the airways of the patient being treated. The compounds of Formula I are administered, e.g., intravenously, intramuscularly, topically, by aerosol inhalation, bucally or orally. The quantity of compound of Formula I effective in achieving the method here claimed is determined by the particular mode of administration and frequency of administration as well as the age and condition of the patient. Generally the amount of compound administered will range from about 0.001 mg to 10 mg per dose given up to three times per day by aerosol inhalation, with a range from about 0.01 mg to 10 mg per dose being preferred. For intravenous administration a dose of about 0.01 to 10

μg/kg/min is administered with intramuscular injection ranging from 0.5 to 15 mg per dose. For oral administration unit doses of from 1 mg to 100 mg given up to three times per day of compounds of Formula I are effective in practicing the method of the present invention. The quantity of compound applied topically is that which will give comparable blood levels of active ingredient when said substance is administered by any of the other various routes of administration.

In practicing the method of treating or preventing the hypersecretion of mucus, the compounds of Formula I are formulated into compositions for administration to humans and animals in unit dosage forms, such as tablets, capsules, pills, powders, granules, sterile parenteral solutions or suspensions, eye drops, oral solutions or suspensions, and oil in water and water in oil emulsions containing suitable quantities of the compound.

For oral administration, either solid or fluid unit dosage forms can be prepared. For preparing solid compositions such as tablets, the compound of Formula I is mixed with conventional ingredients such as talc, magnesium stearate, dicalcium phosphate, magnesium aluminum silicate, calcium sulfate, starch, lactose, acacia, methylcellulose, and functionally similar materials as pharmaceutical diluents or carriers. Capsules are prepared by mixing the compound with an inert pharmaceutical diluent and filling the mixture into a hard gelatin capsule of appropriate size. Soft gelatin capsules are prepared by machine encapsulation of a slurry of the compound with an acceptable vegetable oil, light liquid petrolatum or other inert oil.

Fluid unit dosage forms for oral administration such as syrups, elixirs, and suspensions can be prepared. The forms can be dissolved in an aqueous vehicle together with sugar, aromatic flavoring agents and preservatives to form a syrup. An elixir is prepared by using a hydroalcoholic (ethanol) vehicle with suitable sweeteners such as sugar and saccharin, together with an aromatic flavoring agent.

Suspensions can be prepared with an aqueous vehicle with the aid of a suspending agent such as acacia, tragacanth, methylcellulose and the like.

For parenteral administration, fluid unit dosage forms are prepared utilizing the compound and a sterile vehicle, water being preferred. The pharmaceutically useful compound described herein, depending on the vehicle and concentration used, can be either suspended or dissolved in the vehicle. In preparing solutions the compound can be dissolved in water for injection and filter sterilized before filling into a suitable vial or ampoule and sealing. Advantageously, adjuvants such as a local anesthetic, preservative and buffering agents can be dissolved in the vehicle. To enhance the stability, the composition can be frozen after filling into the vial and the water removed under vacuum. The dry lyophilized powder is then sealed in the vial and an accompanying vial of water for injection is supplied to reconstitute the liquid prior to use. Parenteral suspensions can be prepared in substantially the same manner except that the compound is suspended in the vehicle instead of being dissolved and sterilization cannot be accomplished by filtration. These compounds can be sterilized by exposure to ethylene oxide or an equivalent gas before suspending in the sterile vehicle. Advantageously, a surfactant or wetting agent is included in the composition to facilitate uniform distribution of the compound.

Compositions for inhalation useful in practicing the method of present invention are of three basic types: (1) a powder mixture preferably micropulverized with particle size, preferably from about 2 to 5 microns; (2) an aqueous solution to be sprayed with a nebulizer; (3) an aerosol with volatile propellant in a pressurized container.

The powders are quite simply prepared by mixing a suitable pharmaceutically useful compound of Formula I with a solid base which is compatible with lung tissue, preferably lactose. The powders are packaged in a device adapted to emit a measured amount of powder when inhaled through the mouth.

Aqueous solutions are prepared by dissolving the appropriate compound of the Formula I in water and adding salt to provide an isotonic solution and buffering to a pH compatible with inhalation. The solutions are dispersed in a spray device or nebulizer and sprayed into the mouth while inhaling.

Aerosols are prepared by dissolving an appropriate pharmaceutically useful compound of Formula I in water or ethanol and mixing with a volatile propellant and placing in a pressurized container having a metering valve to release a predetermined amount of material.

The liquefied propellant employed is one which has a boiling point below 65° F. at atmospheric pressure. For use in compositions intended to produce aerosols for medicinal use, the liquefied propellant should be non-toxic. Among the suitable liquefied propellants which may be employed are the lower alkanes containing up to 5 carbon atoms, such as butane and pentane, or a lower alkyl chloride, such as methyl, ethyl or propyl chlorides. Further suitable liquefied propellants are the fluorinated and fluorochlorinated lower alkanes or mixtures thereof, such as, dichlorodifluoromethane, dichlorotetrafluoroethane, trichloromonofluoromethane, dichloromonofluoromethane, monochlorodifluoromethane, trichlorotrifluoroethane, difluoroethane and monochlorotrifluoromethane.

The utility of the method of the present invention has been demonstrated using the mongrel dog model which is generally described by H. G. Johnson et al., Int'l. J. Immunopharmacol., 5: 178 (1983).

As further demonstrated in Example 21 below, the test compound, i.e., 2-butyl-4-methoxy-1-naphthalenol, acetate, is the preferred compound in practicing the present invention. The test compound was effective in blocking baseline secretion in a dose dependent fashion as well as enhanced mucus secretion due to hypoxia or arachidonic acid administration.

The compounds of the present invention are prepared by the method depicted in Reaction Scheme A and Reaction Scheme B.

REACTION SCHEME A

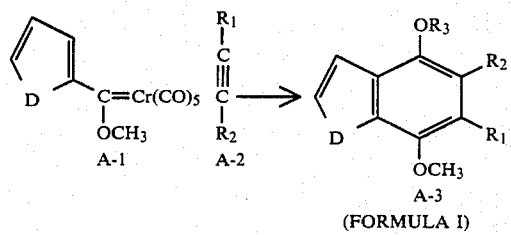

(FORMULA I)

In Reaction Scheme A, a carbene complex of the Formula A-1 is reacted with an acetylene of the Formula A-2 (preferably 1.5 equivalents) in the presence of acetic anhydride (and, preferably triethylamine) with mild heating (preferably having a bath temperature of 60°-65° C.) to yield the Formula A-3 product. This reaction is preferably undertaken in a solvent such as tetrahydrofuran (THF) in an inert atmosphere (e.g., argon).

The process for preparing the compounds of Reaction Scheme A is described more fully in the Examples given below. The chromium complexes within the scope of Formula A-1 are well known and readily available or may be prepared by known means. Thus, pentacarbonyl[aryl(methoxy)carbene]chromium wherein the aryl moiety is phenyl, 2-(N-methylpyrrolyl), 2-furyl, or 2-thienyl are described in E. O. Fisher, J. Organometal. Chem. 16: 29 (1969); K. H. Dötz, et al., Chem. Ber. 111: 2517 (1978); A. Yamashita, et al., Tet. Lett. 23: 3765 (1982); and Citilam, et al., Inorg. Synth. 17: 95 (1977). These compounds are also prepared as described in Preparations 1-4 below.

Similarly, the Formula A-2 alkynes are well known, readily available compounds or may be prepared by known means.

REACTION SCHEME B

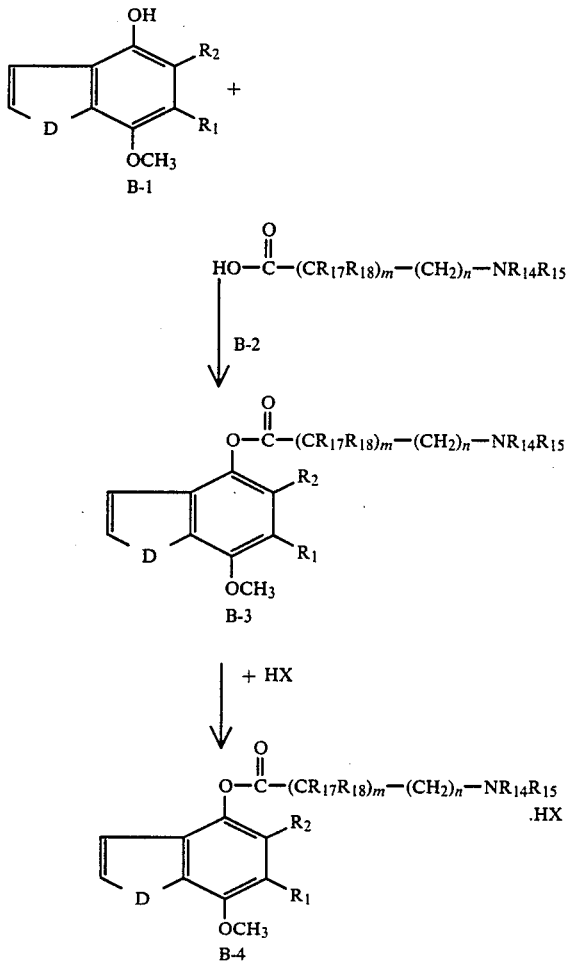

In Reaction Scheme B, the phenolic hydroxyl group of the Formula B-1 compound is acetylated with an amino acid of Formula B-2 (the amino group is either protected or non-protected) using the methodology of A. Hassner, Tet. Lett. 4475 (1978). Specifically, the phenol of Formula B-1 is stirred at room temperature with an amino acid of Formula B-2 and dicyclohexylcarbadinimide in a dry solvent (e.g., methylene chloride, ether) and in the presence of a catalyst (e.g., 4-dimethylaminpyridine, 4-pyrrolidinopyridine) under argon for 24 hours to yield the amine of Formula B-3. When the amino group of the Formula B-2 amino acid is protected, the protecting group is removed by standard methodology. For example, the tert-butyloxycarbonyl group is removed by trifluoroacetic acid in dry methylene chloride, and the benzyl group is removed by catalytic hydrogenation.

The Formula B-3 amine is converted to the Formula B-4 pharmacologically acceptable salt by treatment with the appropriate acid. The acids, which are commonly used for salt formation, include hydrochloric acid, hydrobromic acid, hydroiodic acid, methanesulfonic acid, ethanesulfonic acid, benzenesulfonic acid, phosphoric acid, acetic acid, propionate acid, succinic acid, para-toluenesulfonic acid, maleic acid, tartaric acid, and lactic acid.

Certain compounds of the present invention are preferred. Thus, compounds of the Formula I, when $R_1$ and $R_2$ are ethyl or when $R_2$ is n-butyl and $R_1$ is hydrogen are preferred. More preferred are compounds of this latter class when D is —CH=CH—. Still more preferred, because of their formulation characteristics, are compounds of this latter class, when $R_3$ is —C(O)—$(CR_{17}R_{18})_m$—$(CH_2)_n$—$NR_{14}R_{15}$, —C(O)AA, or —C(O)—PhX—$NH_2$. 1-Acetoxy-2-n-butyl-4-methoxy-naphthalene (Example 3) and 1-acetoxy-2,3-diethyl-4-methoxy-naphthalene (Example 4) are more preferred compounds of this invention. L-Valine, 2,3-diethyl-4-methoxynaphth-1-yl ester, hydrochloride (Example 11), L-Valine, 2-n-butyl-4-methoxynaphth-1-yl ester, hydrochloride (Example 16), and L-Alanine, 2-n-butyl-4-methoxynaphth-1-yl ester, hydrochloride (Example 17) are the most preferred compounds of this invention.

DESCRIPTION OF THE PREFERRED EMBODIMENTS

The present invention is seen more fully by the Examples given below.

PREPARATION 1

Preparation of Pentacarbonyl[2-furyl(methoxy)carbene]chromium

A 500 ml two-necked round-bottomed flask, which is equipped with a stirring bar, a septum cap and an argon-vacuum inlet, is evacuated and filled with argon three times. Freshly distilled tetrahydrofuran (100 ml) and furan (7.5 ml, 0.1 mole) are placed in the flask, which are then cooled at −78° C. with a dry ice-acetone bath. n-Butyl lithium (62 ml, 1.60 mmole/ml, n-hexane solution) is introduced via syringe to the furan solution slowly over a period of 15-20 minutes at −78° C. The resulting solution is warmed to −20° C., and stirred at this temperature for 15 hours (overnight) under argon. The 1000 ml three-necked round bottomed flask is equipped with a stirring bar, a septum cap and an argon-vacuum inlet. Chromium hexacarbonyl (22 g, 0.1 mole) is placed in this flask, which is evacuated and filled with argon three times. Dry ether (200 ml) is added, and to this suspension is added the cooled (−20° C.) solution of 2-lithiofuran at room temperature. During the procedure, chromium hexacarbonyl is dissolved and the solution turns to a deep red color. The resulting solution is stirred at room temperature 1 hour under argon, then concentrated using a rotary evaporator until the solution becomes a tarry residue (during concentration, the bath temperature is kept below 40° C.). The deep red residue is dissolved in 200 ml water and trimethyloxonium tetrafluoroborate (($CH_3)_3O.BF_4$) (solid) is added to the aqueous solution until it becomes slightly acidic (about pH≈5.5) (15 g of ($CH_3)_3O.BF_4$ is used). The aqueous layer is extracted three times with 250 ml of ether, and the combined extracts are washed once with 300 ml of saturated brine, once with 300 ml of saturated sodium carbonate aqueous solution, and again three times with 300 ml of saturated brine, dried over anhydrous sodium sulfate under argon atmosphere, and filtered. The solvent is removed using a rotary evaporator to give a deep red oil, which is dissolved in a small amount of methylene chloride and loaded on a silica gel column (200 g) using a flash chromatography apparatus. Separation of the products by column chromatography is carried out under a nitrogen atmosphere. Elution by 5% ether in n-hexane gives 27.5 g (90.9%) of pentacarbonyl[2-furyl(methoxy)carbene]chromium as deep red crystalline and elution by 20% ether in n-hexane gives 0.9 g (24%) of pentacarbonyl-[2-furyl(methoxybutoxy)carbene]chromium as a deep red oil.

The physical properties of both products are as follows:

Pentacarbonyl[2-furyl(methoxy)carbene]chromium

Mass spectra (m/e): 302, 274, 246, 218, 190, 162, 147, 132, 119, and 52.

IR ($cm^{-1}$): 2060, 1992, 1443, 1386, 1224, and 1218.

$^1$H-NMR (δ, $CDCl_3$): 7.82, 7.02, 6.97, 6.60, 6.56, and 4.81.

Anal. Calc'd. for $C_{11}H_6O_7Cr$: C, 43.72; H, 2.00. Found: C, 44.11; H, 2.17.

Pentacarbonyl[2-furyl(methoxybutoxy)carbene]-chromium

Mass spectra (m/e): 374, 318, 290, 262, 234, 178, 148, and 52.

$^1$H-NMR: 7.83, 6.99, 6.94, 6.59, 6.54, 5.11, 3.43, 3.35, and 2.10–1.70.

PREPARATION 2

Preparation of Pentacarbonyl[2-Thienyl(methoxy)carbene]-chromium

A 500 ml two-necked round-bottomed flask, which is equipped with a stirring bar, a septum cap and an argon-vacuum inlet, is evacuated and filled with argon three times. Freshly distilled tetrahydrofuran (100 ml) and thiophene (8.01 ml) are placed in the flask, which is cooled to −78° C. with a dry ice-acetone bath. n-Butyl lithium (62 ml, 1.60 mmole/ml, n-hexane solution) is introduced via syringe to the thiophene solution slowly over a period of 20 minutes at −78° C. The resulting solution is stirred at −30° C. for 10 hours under argon. The 1000 ml three-necked round-bottomed flask is equipped with a stirring bar, a septum cap and an argon-vacuum inlet, and chromium hexacarbonyl (22 g, 0.1 mole) is placed in this flask, which is evacuated and filled with argon three times. Dry ether (200 ml) is introduced to the flask. A solution of 2-lithio-thiophene (−30° C.) is introduced via syringe to the suspension of chromium hexacarbonyl in ether at room temperature. During this procedure most of chromium hexacarbonyl is dissolved and the solution turns to a deep red color. The resulting solution is stirred at room temperature for 1 hour under argon, and concentrated using a rotary evaporation (bath temperature is kept below 40° C.) until the solution becomes a thick tarry residue. The black residue is dissolved in 200 ml water and ($CH_3)_3O.BF_4$ (solid) is added to the solution until it becomes slightly acidic (about pH≈5.5). The aqueous solution is extracted three times with 250 ml of ether and the extracts are combined, washed once with 300 ml of saturated brine, once with 300 ml of saturated sodium bicarbonate aqueous solution and three times with 300 ml of saturated brine, and dried over anhydrous sodium sulfate under a stream of argon. The solution is filtered and the solvent is removed using a rotary evaporator (the bath temperature is kept below 40° C.). The dark red oily residue is dissolved in a small amount of methylene chloride and loaded on a silica gel column (200 g) using flash chromatography apparatus under a nitrogen atmosphere. Elution by 5% ether in n-hexane gives 25.8 g (81.0%) of deep red crystals of pentacarbonyl[2-thienyl(methoxy)carbene]chromium and 1.22 g (3.13%) of pentacarbonyl[2-thienyl(methoxybutoxy)-carbene]chromium as deep red crystals.

The physical properties of both products are as follows:

Pentacarbonyl[2-thienyl(methoxy)carbene]chromium

Mass spectra (m/e): 318, 290, 262, 234, 206, 178, 163, 148, 135, and 52.

IR ($cm^{-1}$): 2056, 1991, 1402, 1352, and 1238.

$^1$H-NMR (δ, $CDCl_3$): 8.28, 8.22, 7.73, 7.67, 7.23, 7.18, and 4.83.

Anal. Calc'd. for $C_{11}H_6O_6SCr$: C, 41.52; H, 1.90; S, 10.08. Found: C, 41.81; H, 2.04; S, 9.25.

Pentacarbonyl[2-thienyl(methoxybutoxy)carbene]-chromium

Mass spectra (m/e) calc'd. for $C_{15}H_{14}O_7SCr$: 389.987. Found: 389.985.

IR ($cm^{-1}$): 2059, 1989, 1407.

$^1$H-NMR (δ, $CDCl_3$): 8.28, 8.23, 7.71, 7.65, 7.25–7.15, 5.14, 3.49, 3.36, and 2.25–1.70.

Anal. Calc'd. for $C_{15}H_{14}O_7SCr$: C, 46.15; H, 3.61; S, 8.22. Found: C, 46.72; H, 3.68; S, 7.71.

PREPARATION 3

Preparation of Pentacarbonyl[phenyl(methoxy)carbene]chromium

To a suspension of 22 g (0.1 mole) of chromium hexacarbonyl in ether is slowly added phenyllithium (51 ml, 0.1 mole, cyclohexane:ether solution) via syringe over a period of 15–20 minutes under argon at room temperature, and the resulting deep red solution is stirred at room temperature for 1 hour. The solvent is removed under reduced pressure (bath temperature should be below 40° C.), and the black residue is dissolved in 200 ml water. ($CH_3)_3O.BF_4$ (about 15 g) is added portionwise to the solution until it becomes slightly acidic (pH≈5.5). The aqueous layer is extracted three times with 200 ml of ether, and the combined etheral extracts are washed once with 300 ml of saturated brine solution, once with 300 ml of saturated sodium carbonate solution, and three times with 300 ml of saturated brine solution, dried over anhydrous sodium sulfate and filtered. The solvent is removed using a rotary evaporator and the deep red tarry residue is purified by a silica gel column (200 g) using flash chromatography. Elution by approx. 10% ether in n-hexane gives a deep red syrup, which is solidified upon cooling. Recrystallization from pet-ether at −70° C. gives 25.12 g (80.5%) of pentacarbonyl[phenyl(methoxy)carbene]-chromium as deep red crystalline.

The physical properties of the product are consistent with those described in the literature.

PREPARATION 4

Preparation of Pentacarbonyl[2-N-methylpyrrolyl(methoxy)carbene]-chromium

A 500 ml two-necked round-bottomed flask, which is equipped with a stirring bar, a septum cap and an argon-vacuum inlet, is evacuated and filled with argon three times. Tetrahydrofuran (100 ml) and N-methylpyrrole (9.0 ml, 0.1 mole) are placed in this flask, which is then cooled at −78° C. with dry ice-acetone bath. n-Butyllithium (62 ml, 1.60 mmole/1 ml n-hexane solution) is introduced via syringe to the pyrrole solution slowly over a period of 15 minutes at −78° C. The resulting pale yellow solution is warmed to −20° C., and stirred at this temperature for 15 hours under argon. A 1000 ml three-necked round-bottomed flask is equipped with a stirring bar, a septum cap and an argon-vacuum inlet, and chromium hexacarbonyl (22 g, 0.1 mole) is placed in this flask, which is evacuated and filled with argon three times. Dry ether (200 ml) is added and to this suspension is added the cooled (−20° C.) solution of 2-lithio-N-methylpyrrole at room temperature via syringe. During this procedure, most of the chromium hexacarbonyl is dissolved and the solution is stirred at room temperature for 1 hour under argon, and then concentrated using a rotary evaporator until the solution becomes a tarry residue (during concentration, bath temperature should be below 40° C.). The deep red residue is dissolved in 200 ml water and $(CH_3)_3O.BF_4$ (solid) is added to the solution until it becomes slightly acidic (about pH≈5.5) (15 g of $(CH_3)_3O.BF_4$ is used). The aqueous solution is extracted three times with 250 ml of ether, and the combined extracts are washed once with 300 ml of saturated brine, once with 300 ml of saturated sodium carbonate, and three times with 300 ml of saturated brine, and finally dried over anhydrous sodium sulfate under argon atmosphere and filtered. The solvent is removed using a rotary evaporator (bath temperature should be below 40° C.). The dark red residue is dissolved in a small amount of methylene chloride, and loaded on a silica gel column (200 g) using flash chromatography apparatus. Separation of the product by column chromatography is carried out under nitrogen atmosphere. Elution by 10% ether in n-hexane gives a small amount of pentacarbony[n-butyl(methoxy)carbene]chromium as a yellow oil, elution by 40% ether in n-hexane gives 19.63 g (62.3%) of pentacarbonyl[2-N-methylpyrrole(methoxy)carbene]-chromium as orange crystals. Further elution by a 1:1 mixture of ether and n-hexane gives a small amount of pentacarbonyl[2-methylpyrrole(methoxybutoxy)carbene]chromium as a deep red oil.

The physical properties of the desired product are as follows:

Mass spectra (m/e): 315, 287, 259, 231, 203, 175, 160, 145, 132, and 52.

IR (cm$^{-1}$): 2053, 1984, 1400, 1343, and 1323.

$^1$H-NMR (δ, CDCl$_3$): 7.75, 7.70, 6.79, 6.29, 6.27, 4.71, and 3.73.

Anal. Calc'd. for $C_{12}H_9NO_6Cr$: C, 45.75; H, 2.88; N, 4.44. Found: C, 45.82; H, 3.02; N, 4.38.

EXAMPLE 1

5-Butyl-7-methoxy-4-benzofuranol (Formula I: D is —O—, $R_3$ is hydrogen, $R_2$ is n-butyl, and $R_1$ is hydrogen)

Reaction of pentacarbonyl[2-furyl(methoxy)carbene]chromium with 1-hexyne.

A mixture of 1.0 g (3.3 mmole) of the carbene complex and 1 ml (2.6 eq) of 1-hexyne in tetrahydrofuran is heated at 65° C. for 6 hours under argon atmosphere. After cooling the solvent is removed and the product is purified by flash column chromatography (silica gel), eluting with 5% ether in n-hexane, to give 552 mg (76.0%) of the title product as a colorless oil, which solidifies upon cooling.

Physical characteristics of the product are as follows:

Mass spectra (m/e): 220, 205, 177, and 163.

IR (cm$_{-1}$): 3200, 1634, 1465, and 1346.

$^1$H-NMR (δ, CDCl$_3$): 7.52, 6.77, 6.56, 4.65, 3.95, 2.80–2.50, and 1.90–0.85.

Anal. Calc'd. for $C_{13}H_{16}O_3$: C, 70.88; H, 7.32. Found: C, 71.01; H, 7.36.

EXAMPLE 2

5-Butyl-7-methoxy-benzo(b)thiophen-4-ol (Formula I: D is —S—, $R_3$ is hydrogen, $R_2$ is n-butyl, and $R_1$ is hydrogen)

Reaction of pentacarbony[2-thienyl(methoxy)carbene]chromium with 1-hexyne.

A solution of 200 mg (0.62 mmole) of the carbene complex and 1-hexyne (1.5 eq) in tetrahydrofuran, prepared under argon, is heated at 60° C. for 4 hours. After the solution is cooled to room temperature, the reaction mixture is stirred at room temperature overnight under argon. The solvent is removed under reduced pressure, and the residue is loaded on a silica gel plate (1500 micron) for thick layer chromatography. Developing by n-hexane:ether (4:1 mixture) three times yields 64 mg (43.8%) of the title product.

The physical characteristics of the products are as follows:

Mass spectral (m/e): 236, 221, 193, and 179.

IR (cm$^{-1}$) 3282, 1579, 1516, 1465, and 1447.

$^1$H-NMR (δ, CDCl$_3$): 7.50–7.20, 6.54, 3.93, 2.75–2.50, and 2.00–0.75

Anal. Calc'd. for $C_{13}H_{16}O_2S$: C, 66.07; H, 6.83; S, 13.57. Found: C, 65.70; H, 6.86; S, 13.19.

EXAMPLE 3

2-Butyl-4-methoxy-1-naphthalenol, acetate (Formula I: D is —CH=CH—; $R_3$ is $CH_3$—C(O)—; $R_2$ is n-butyl, and $R_1$ is hydrogen)

Reaction of pentacarbonyl[phenyl(methoxy)carbene]chromium with 1-hexyne.

Part A

A mixture of the carbene complex (1.0 g, 3.2 mmole), 1-hexyne (2.6 eq), acetic anhydride (1.0 eq) and triethylamine (1.0 eq) in tetrahydrofuran (90 ml) is heated at 65° C. under argon atmosphere for 1 hour. The solution is cooled and concentrated to give a black residue which is chromatographed through a silica gel (200 g) column using a flash chromatography. Elution by 10% ether in n-hexane gives 715 mg (82.2%) of the title product which solidified. Recrystalization from pet-ether gave white crystals, mp 49° C.

The physical properties are as follow:
Mass spectra (m/e): 272, 230, and 187.
Calc'd. for $C_{17}H_{20}O_3$: 272.1412. Found: 272.1412.
IR (cm$^{-1}$): 1761, 1597, 1370, 1202, 1162, and 765.
$^1$H-NMR ($\delta$, CDCl$_3$): 8.25–8.10, 7.75–7.40, 6.65, 3.98, 2.75–2.50, 2.45, and 1.80–0.80.
Anal. Calc'd. for $C_{17}H_{20}O_3$: C, 74.97; H, 7.41. Found: C, 75.02; H, 7.40.

Part B

Alternatively, a mixture of 2.0 g (6.4 mmole) of the carbene complex, acetylene (2.6 eq) and acetic acid in tetrahydrofuran is heated at 65° C. for 2 hours under an argon atmosphere. After cooling the reaction solution is concentrated and the black residue is loaded on a silica gel (200 g) column for a flash chromatography. Elution by 10% ether in n-hexane gives 895 mg (51.4%) of the title product.

The physical properties of the product is the same as described above.

EXAMPLE 4

2,3-Diethyl-4-methoxy-1-naphthalenol, acetate (Formula I: D is —CH=CH—, $R_3$ is CH$_3$—C(O)—, $R_2$ and $R_1$ are ethyl)

Reaction of pentacarbonyl[phenyl(methoxy)carbene]chromium with 3-hexyne in the presence of acetic anhydride and triethylamine.

A mixture of the carbene complex (2.0 g, 6.4 mmole), 3-hexyne (2.0 ml, 2.8 eq), acetic anhydride (0.65 ml, 1.1 eq) and triethylamine (0.9 ml, 1.0 eq) in tetrahydrofuran (180 ml) is heated at 65° C. for 2 hours under argon atmosphere. After cooling the solvent is removed and the black residue is loaded on silica gel column for 74.7% of the title product as a yellow oil.

Physical characteristics are as follows:
Mass spectra (m/e): 272, 230, and 215.
Calc'd. for $C_{17}H_{20}O_3$: 272.1412. Found: 272.1412.
IR (cm$^{-1}$): 1762, 1594, 1357, 1208, and 1096.
$^1$H-NMR ($\delta$, CDCl$_3$): 8.10–7.85, 7.70–7.30, 3.94, 2.47, 2.80–2.50, 1.25, and 1.20.
Anal. Calc'd. for $C_{17}H_{20}O_3$: C, 74.97; H, 7.40. Found: C, 75.35; H, 7.56.

EXAMPLE 5

4-Methoxy-2,3-diphenyl-1-naphthalenol, acetate (Formula I: D is —CH=CH—, $R_3$ is CH$_3$C(O)—, $R_2$ and $R_1$ are phenyl)

Reaction of pentacarbonyl[phenyl(methoxy)carbene]chromium with diphenylacetylene in the presence of acetic anhydride and triethylamine.

A mixture of the carbene complex (1.0 g, 3.2 mmole), acetylene (1.0 g, 1.8 eq), acetic anhydride (0.3 ml, 1.0 eq) and triethylamine (0.45 ml, 1.0 eq) in 90 ml of tetrahydrofuran is heated at 65° C. for 2 hours under an argon atmosphere. After cooling, the reaction solution is concentrated to give a black residue, which is chromatographed through a silica gel (200 g) column using a flash chromatography. Elution by 20% ether in n-hexane gives 620 mg (53.0%) of the title product as a yellow oil.

Physical characteristics are as follows:
Mass spectra (m/e): 368, 326, and 311.
Calc'd. for $C_{25}H_{20}O_3$: 368. 1412. Found: 368.1422.
IR (cm$^{-1}$): 1768.
$^1$H-NMR ($\delta$, CDCl$_3$): 8.25–8.00, 7.80–7.40, 7.15, 3.51, and 2.04.
Anal. Calc'd. for $C_{25}H_{20}O_3$: C, 81.40; H, 5.47. Found: C, 81.10; H, 5.60.

EXAMPLE 6

5-Butyl-7-methoxy-1-methyl-1H-Indol-4-ol, acetate (ester) (Formula I: D is =N(CH$_3$); $R_3$ is CH$_3$C(O)—, $R_2$ is n-butyl, $R_1$ is hydrogen)

Reaction of pentacarbonyl[2-(N-methyl)pyrrolyl(methoxy)carbene]chromium with 1-hexyne in the presence of acetic anhydride and triethylamine.

A mixture of the carbene complex (2.0 g, 6.4 mmole), acetylene (2 ml, 2.6 eq), acetic anhydride, (0.7 ml, 1.1 eq) and triethylamine (0.9 ml, 1.1 eq) in 180 ml of tetrahydrofuran is heated at 65° C. under an argon atmosphere for 1–2 hours. The solution is cooled and concentrated. The residue is loaded on a silica gel (480 ml) column for flash chromatography, yielding the litle product as a brown oil.

Physical characteristics are as follows:
Mass spectra (m/e): 275, 233, and 190.
IR (cm$^{-1}$): 1759, 1581, 1502, 1207, and 1013.
$^1$H-NMR ($\delta$, CDCl$_3$): 6.84, 6.39, 6.14, 3.97, 3.88, 2.60–2.30, 2.36, and 1.75–0.75.
Anal. Calc'd. for $C_{16}HH_{21}NO_3$: C, 69.79; H, 7.69; N, 5.09. Found: C, 70.00; H, 7.81; N, 5.00.

EXAMPLE 7

5,6-Diethyl-7-methoxy-1-methyl-1H-indol-4-ol, acetate (ester) (Formula I: D is =N(CH$_3$); $R_3$ is CH$_3$C(O)—, $R_2$ and $R_1$ are ethyl)

Reaction of pentacarbonyl[2-N-methyl)pryyolyl(methoxy)carbene]chromium with 3-hexyne in the presence of acetic anhydride.

Part A

A mixture of the carbene complex (2.5 g, 7.9 mmole), 3-hexyne (2.5 ml, 2.8 eq) and acetic anhydride (0.75 ml, 1.1 eq) in 200 ml of tetrahydrofuran is heated at 60°–65° C. for 5 hours under argon. The reaction solution is cooled and concentrated. The black residue (one spot on TLC) is chromagraphed through a silica gel (220 g) column using a flash chromatography. Elution by 25% ether in n-hexane gives 2.17 g (42.4%) of the title product as a yellow oil.

The physical characteristics are as follows:
Mass spectra (m/e): 275, 233, and 218.
Calc'd. for $C_{16}H_{21}NO_3$: 275.1521. Found: 275.1515.
IR (cm$^{-1}$): 1761, 1488, 1295, 1216, and 1196.
$^1$H-NMR ($\delta$, CDCl$_3$): 6.84, 6.14, 3.97, 3.85, 2.78–3.62, 1.22, and 1.44.
Anal. Calc'd. for $C_{16}H_{21}NO_3$: C, 69.79; H, 7.69; N, 5.09. Found: C, 69.60; H, 7.46; N, 5.10.

Part B

Alternatively, a mixture of 1.5 g (4.8 mmole) of the carbene complex, 1.5 ml of 3-hexyne, 0.9 ml of acetic anhydride and 0.7 ml of triethylamine in 130 ml of tetrahydrofuran is heated at 65° C. for 6 hours under a 1.3 ml argon atmosphere. The reaction is carried out in the same manner described above. Silica gel flash column chromatography yields 590 mg (44.7%) of the title product.

EXAMPLE 8

7-Methoxy-1-methyl-5,6-diphenyl-1H-indol-4-ol, acetate (ester) (Formula I: D is $=N(CH_3)$; $R_3$ is $CH_3C(O)-$; $R_1$ and $R_2$ are phenyl)

Reaction of pentacarbonyl[2-(N-methyl)pyrrolyl(methoxy)carbene]chromium with diphenyl acetylene in the presence of acetic anhydride and triethylamine.

A mixture of the carbene complex (1.5 g, 4.8 mmole), acetylene (1.8 eq), acetic anhydride (2.0 eq) and triethylamine (1.0 eq) in tetrahydrofuran (150 ml) is heated at 65° C. under argon atmosphere for 5 hours. After cooling, the solvent is removed and the product is purified by a silica gel flash column chromatography. Elution by 50% ether in n-hexane gives 390 mg (22.0%) of the title product as yellow crystals.

The physical properties are as follows:
Melting point: 158°–159.5° C.
Mass spectra (m/e): 371, 329, and 314.
Calc'd. for $C_{24}H_{21}NO_3$: 371.1521. Found: 371.1511.
IR ($cm^{-1}$): 1761, 1599, and 1202.
$^1$H-NMR ($\delta$, $CDCl_3$): 7.13, 6.99, 6.32, 4.03, 3.36, and 2.01.
Anal. Calc'd. for $C_{24}H_{21}NO_3$: C, 77.61; H, 5.70; N, 3.77. Found: C, 77.27; H, 5.73; N, 3.67.

EXAMPLE 9

5-Butyl-7-methoxy-4-benzofuranol, acetate (Formula I: D is $-O-$, $R_3$ is $CH_3C(O)-$, $R_2$ is n-butyl, $R_1$ is hydrogen)

Reaction of pentacarbonyl[2-furyl(methoxy)carbene]chromium with 1-hexyne in the presence of acetic anhydride and triethylamine.

A mixture of the carbene complex (1 g, 3.3 mmole), 1-hexyne (0.57 ml, 1.5 eq), acetic anhydride (1.0 eq) and triethylamine (1.0 eq) in tetrahydrofuran (90 ml), prepared under argon atmosphere, is heated at 65° C. under argon for 6 hours. An additional 1-hexyne (1.0 eq) is added to the reaction mixture, which is heated at 65° C. for an additional 17 hours. The resulting black solution is cooled and the solvent is removed by using a rotary-evaporator. The black residue is chromatographed through flash column chromatography (250 g of silica gel). Elution by 30% ether in n-hexane yields 590 mg (68.2%) of the title product as a pale purple solid.

Physical characteristics are as follows:
Melting point: 49°–50° C.
Mass spectra (m/e): 262, 220, and 177.
Calc'd. for $C_{15}H_{18}O_4$: 262.1205. Found: 262.1211.
IR ($cm^{-1}$): 1761, 1490, 1446, 1349, and 1208.
$^1$H-NMR ($\delta$, $CDCl_3$): 7.54, 6.63, 6.55, 3.99, 2.75–2.45, 2.37, and 1.75–0.80.
Anal. Calc'd. for $C_{15}H_{18}O_4$: C, 68.69; H, 6.92. Found: C, 68.80; H, 7.00.

EXAMPLE 10

5-Butyl-7-methoxy-benzo(b)thiophen-4-ol, acetate (Formula I: D is $-S-$; $R_3$ is $CH_3C(O)-$; $R_2$ is n-butyl; $R_1$ is hydrogen)

Reaction of pentacarbonyl[2-thienyl(methoxy)carbene]chromium with 1-hexyne in the presence of acetic anhydride and triethylamine.

A mixture of the carbene complex (1.0 g, 3.1 mmole), 1-hexyne (0.53 ml, 1.5 eq), acetic anhydride (1.0 eq), and triethylamine (1.0 eq) in tetrahydrofuran (90 ml), prepared under an argon atmosphere, is heated at 65° C. under argon. After heating at this temperature for 4 hours, an additional 0.26 ml (1.0 eq) of 1-hexyne is introduced to the reaction mixture, which is heated at 65° C. under argon for an additional 16 hours. The resulting black solution is cooled, and concentrated to dryness by aid of a rotary evaporator. The black residue is chromatographed by using flash column chromatography (300 g of silica gel). Elution by 15% ether in n-hexane gives 570 mg (66.1%) of the title product as a pale yellow solid.

Physical characterisitics are as follows:
Melting point: 51°–52° C. (recrystallized from cold pet ether/n-hexane).
Mass spectra (m/e): 278, 236, and 193.
IR ($cm^{-1}$): 1762, 1510, 1465, 1436, 1375, and 1202.
$^1$H-NMR ($\delta$, $CDCl_3$): 7.36, 7.13, 6.61, 3.96, 2.39, 2.75–2.40, and 1.80–0.80.
Anal. Calc'd. for $C_{15}H_{18}O_3S$: C; 64.49; H, 6.55; S, 11.52. Found: C, 64.75; H, 6.55; S, 11.69.

EXAMPLE 11

L-Valine, 2,3-diethyl-4-methoxynaphth-1-yl ester and its hydrochloric acid salt (Formula I: D is $-CH=CH-$, $R_3$ is $-C(O)-AA$, $-C(O)-AA$ is the acyl portion of L-Valine, $R_2$ is ethyl, $R_1$ is ethyl)

Part A

Dry methylene chloride (15 ml) is introduced to a mixture of 2,3-diethyl-4-methoxynaphthol (100 mg, 0.44 mmole), t-Boc-L-valine (2 eq, 189 mg, 0.88 mmole), dicyclohexylcarbodiimide (2 eq, 180 mg, 0.88 mmole), and 4-dimethylaminopyridine (1 eq, 55 mg, 0.44 mmole) at room temperature under an argon atmosphere. The resulting solution is stirred at room temperature under argon for 20 hours, then diluted with 100 ml of methylene chloride. The white precipitate is removed by filtration, and the filtrate washed once with 50 ml of water, twice with 50 ml of saturated aqueous sodium bicarbonate solution, and then three times with 50 ml of water. The extracts are dried over anhydrous sodium sulfate, filtered and concentrated. Thick layer chromatography (silica gel), developed by 1:4 mixture of ether and n-hexane, isolates 200 mg (quantitative yield) of the t-Boc-L-valine,2,3-diethyl-4-methoxynaphth-1-yl ester as a colorless syrup.

Physical characteristics are as follows:
$^1$H-NMR ($\delta$, $CDCl_3$): 8.10–7.90, 7.70–7.50, 7.50–7.30, 5.20–4.90, 4.70–4.50, 3.93, 3.00–2.50, 1.49, and 1.40–1.00.

Part B

Trifluoroacetic acid (50 ml) is added slowly to an ice bath solution of t-Boc-L-valine,2,3-diethyl-4-methoxynaphth-1-yl ester (2.68 g, 6.2 mmole) in dry methylene chloride (70 ml) under argon. The ice bath is removed and the resulting yellow solution stirred at room temperature for 1 hour under argon. The solvents are removed using a rotary evaporator and the residue is dissolved in methylene chloride. The methylene chloride extracts are washed with an aqueous sodium bicarbonate solution once and three times with 200 ml of water, dried over anhydrous sodium sulfate, filtered and concentrated. The residue is chromatographed by using a silica gel (200 g) flash column and eluted by 10% methanol in methylene chloride, giving 2.09 g of L-valine,2,3-diethyl-4-methoxynaphth-1-yl ester (quantitative yield) as a colorless oil.

Physical characteristics are as follows:
Mass spectra (m/e): 329, 230, 214, and 72.

IR(cm$^{-1}$): 3394, 1755, 1359, 1133.

$^1$H-NMR ($\delta$, CDCl$_3$): 8.15–7.90, 7.70–7.30, 3.94, 3.86, 3.00–2.45, and 1.40–1.00.

Anal. Calc'd. for C$_{20}$H$_{27}$NO$_3$: 329.1991. Found: 329.1993.

The deprotected L-valine,2,3-diethyl-4-methoxynaphth-1-yl ester is dissolved in a small amount of dry methylene chloride and treated with hydrochloric acid saturated anhydrous ether. Recrystallization from ether in n-hexane gives the hydrochloric acid salt.

Physical characteristics are as follows:

Melting point: 183°–186° C.

Mass spectra (m/e): 329, 230, 215, and 72.

IR (cm$^{-1}$): 1761, 1463, 1357, and 1191.

Anal. Calc'd. for C$_{20}$H$_{28}$NO$_3$Cl: C, 65.65; H, 7.71: N, 3.83; Cl, 9.69. Found: C, 65.70; H, 8.01; N, 3.78; Cl, 9.54.

EXAMPLE 12

L-Alanine, 2,3-diethyl-4-methoxynaphth-1-yl ester (Formula I: D is —CH=CH—, R$_3$ is —C(O)AA, —C(O)AA is the acyl portion of L-alanine, R$_2$ is ethyl, R$_1$ is ethyl).

Part A

Dry methylene chloride (35 ml) is added to a mixture of 2,3-diethyl-4-methoxynaphthol (200 mg, 0.87 mmole), t-Boc-L-Alanine (2 eq, 326 mg, 1.74 mmole), dicyclohexylcarbodiimide (2 eq, 360 mg, 1.74 mmole) and 4-dimethylaminpyridine (1 eq, 110 mg, 0.87 mmole) at room temperature under an argon atmosphere. The resulting solution is stirred at room temperature under argon for 20 hours, then diluted with methylene chloride. The white precipitate is removed by filtration, and the filtrate is washed once with water, twice with saturated aqueous sodium bicarbonate solution and three times with water. The extracts are dried over anhydrous sodium sulfate, filtered and concentrated. Thick layer chromatography (2000 micron, silica gel), developed by 1:4 mixture of ether-n-hexane, isolates 326 mg (93.5%) of t-Boc-L-Alanine, 2,3-diethyl-4-methoxynaphth-1-yl ester as a colorless oil.

Physical characteristics are as follows:

Mass spectra (m/e): 401, 328, 230, and +215.

$^1$H-NMR ($\delta$, CDCl$_3$): 8.15–7.85, 7.75–7.55, 7.50–7.30, 5.20–5.00, 4.90–4.60, 3.93, 3.05–2.45, 1.70, 1.48, 1.24 and 1.18.

Part B

Trifluoroacetic acid (50 ml) is introduced slowly to a cooled ice bath solution of t-Boc-L-Alanine,2,3-diethyl-4-methoxynaphth-1-yl ester (2.70 g, 6.70 mmole) in dry methylene chloride (70 ml) under argon. The ice bath is removed and the resulting yellow solution is stirred at room temperature for 1.5 hours under argon. The solvents are removed using a rotary evaporator and the residue is dissolved in 400 ml of methylene chloride. The methylene chloride extracts are washed once with aqueous sodium bicarbonate, three times with water, dried over anhydrous sodium sulfate, filtered and concentrated. The residue is chromatographed through a silica gel (200 g) flash column, and eluted by 2% methanol in methylene chloride to give 1.97 g (97.5%) of a yellow oil.

Physical characteristics are as follows:

Mass spectra (m/e): 301, 230, 215, and +44.

IR (cm$^{-1}$): 3482, 1757, 1660, 1451, 1376, 1359, and 1153.

$^1$H-NMR ($\delta$, CDCl$_3$): 8.20–7.95, 7.70–7.30, 4.05, 3.93, 3.00–2.50, 1.67, 1.18, and 1.15.

Anal. Calc'd. for C$_{18}$H$_{23}$NO$_3$: 301.1678. Found: 301.1685.

EXAMPLE 13

L-Phenylalanine, 2,3-diethyl-4-methoxynaphth-1-yl ester (Formula I: D is —CH=CH—, R$_3$ is —C(O)AA, —C(O)AA is the acyl portion of L-phenylalanine, R$_2$ is ethyl, R$_1$ is ethyl)

Part A

Dry methylene chloride (100 ml) is introduced to a mixture of 2,3-diethyl-4-methoxynaphthol (1 g, 4.3 mmole), t-Boc-L-phenylalanine (1.5 eq, 1.7 g, 6.4 mmole), dicyclohexylcarbodiimide (1.5 eq, 1.4 g, 6.4 mmole), and 4-dimethylaminpyridine (0.37 eq, 0.2 g, 1.6 mmole) under an argon atmosphere at room temperature. The resulting solution is stirred at room temperature for 20 hours under argon. The white precipitates are removed by filtration and the filtrate washed twice with 100 ml of saturated aqueous sodium bicarbonate solution and three times with 100 ml of water, dried over anhydrous sodium sulfate, filtered and concentrated. The residue is chromatographed through a silica gel (200 g) flash column, and eluted by 10–15% ether in n-hexane to give 1.7 g of t-Boc-L-phenylalanine, 2,3-diethyl-4-methoxynaphth-1-yl ester as a colorless amorphous crystal.

Physical characteristics are as follows:

Mass spectra (m/e): 404, 230, and +215.

IR (cm$^{-1}$): 1762, 1716, 1689, 1455, and 1367.

$^1$H-NMR ($\delta$, CDCl$_3$): 8.15–7.90, 7.60–7.30, 5.20–4.90, 3.93, 3.50–3.20, 3.00–2.40, 1.44, and 1.40–1.00.

Anal. Calc'd. for C$_{29}$H$_{35}$NO$_5$: C, 72.93; H, 7.39; N, 2.93. Found: C, 72.63; H, 7.45; N, 2.88.

Part B

A solution of the t-Boc-L-phenylalanine, 2,3-diethyl-4-methoxynaphth-1-yl ester (1.6 g, 3.4 mmole) in dry methylene chloride (40 ml), prepared under argon, is treated with trifluoroacetic acid (10 ml) at 0° C. (ice bath), and the yellow solution stirred at 0° C. for 30 minutes under argon. The ice bath is removed and the solution is stirred at room temperature for an additional 45 minutes under argon. The solvents are removed using a rotary evaporator and the residue is dissolved in 300 ml of methylene chloride. The methylene chloride extracts are washed three times with 200 ml of water, dried over anhydrous sodium sulfate, filtered and concentrated. The residue is chromatographed through a silica gel (200 g) flash column and eluted by 1–2% methanol in methylene chloride to give 1.11 g (86.7%) of L-phenylalanine, 2,3-diethyl-4-methoxynaphth-1-yl ester as a pale yellow oil.

Physical characteristics are as follows:

Mass spectra (m/e): 377, 230, 215, 120, and 91.

IR (cm$^{-1}$): 3380, 3320, 3060, 3030, 2870, 2830, 2770, 1755, 1685, 1660, 1595, 1575, 1495, 1455, 1360, 1145, 1105, 1020, 760, 745, and 700.

$^1$H-NMR ($\delta$, CDCl$_3$): 8.15–7.85, 7.50–7.25, 4.30–4.05, 3.94, 3.50–2.95, 2.95–2.45, 1.24 and 1.16.

Anal. Calc'd. for C$_{24}$H$_{27}$NO$_3$: 377.1991. Found: 377.1988.

In accordance with the procedure of Example 13, Part B, the free amine is converted to the hydrochloric acid salt and recrystallized from absolute ethanol and ether in n-hexane.

Physical characteristics are as follows:
Melting point: 218°–200° C.
Mass spectra (m/e): 377, 249, 230, 215, and 120.
IR (cm$^{-1}$): 3060, 3030, 2720, 2630, 1755, 1595, 1575, 1510, 1495, 1200, 760, and 705.
Anal. Calc'd. for $C_{24}H_{28}ClNO_3$: C, 69.64; H, 6.82; N, 3.38; Cl, 8.57. Found: C, 69.48; H. 6.63; N, 4.06; Cl, 8.03

EXAMPLE 14

3-(N,N-Diethylamino) propionic acid, 2,3-diethyl-4-methoxynaphth-1-yl ester. (Formula I: D is —CH=CH—, $R_3$ is —C(O)—$(CR_{17}R_{18})_m$—$(CH_2)_n$—$NR_{14}R_{15}$, $R_2$ is ethyl, $R_1$ is ethyl, $R_{17}$ is hydrogen, $R_{18}$ is hydrogen, $R_{14}$ is ethyl, $R_{15}$ is ethyl, n is 1, and m is 1)

Dry methylene chloride (30 ml) and triethylamine (0.33 ml, 2.34 mmole) are added to a mixture of 2,3-diethyl-4-methoxynaphthol (180 mg, 0.78 mmole), dimethylamino propionic acid hydrochloride (2 eq, 283 mg, 1.56 mmole), dicyclohexylcarbodiimide (2 eq, 322 mg, 1.56 mmole) and 4-dimethylaminpyridine (1 eq, 95 mg, 0.78 mmole) at room temperature under argon, and the resulting suspension is stirred at room temperature under argon for two days. The white precipitate is removed by filtration, and the filtrate is concentrated. Thick layer chromatography (silica gel, 2000 micron) developed by a 9:1 mixture of ether and n-hexane isolates 144 mg (51.8%) of 3-(N,N-diethylamino) propionic acid, 2,3-diethyl-4-methoxynaphth-1-yl ester as a colorless oil.

Physical characteristics are as follows:
Mass spectra (m/e): 357, 284, 230, 215, and 86.
IR (cm$^{-1}$): 1758, 1660, 1595, 1451, and 1360.
$^1$H-NMR ($\delta$, $CDCl_3$): 8.10–7.70, 7.50–7.30, 3.94, 3.00–2.45, and 1.40–0.90.
Anal. Calc'd. for $C_{22}H_{31}O_3N$: 357.2304. Found: 357.2292.

EXAMPLE 15

N,N-Dimethylamino acetic acid, 2,3-diethyl-4-methoxynaphth-1-yl ester (Formula I: D is —CH=CH—, $R_3$ is C(O)—$(CR_{17}R_{18})_m$—$(CH_2)_n$—$NR_{14}R_{15}$, $R_2$ is ethyl, $R_1$ is ethyl, $R_{17}$ is hydrogen, $R_{18}$ is hydrogen, $R_{14}$ is methyl, $R_{15}$ is methyl, n is 0, and m is 1)

Triethylamine (3 eq) and dry methylene chloride (150 ml) are introduced to a mixture of 2,3-diethyl-4-methoxynaphthol (1.59 g, 6.5 mmole), dimethylamino acetic acid hydrochloride (2 eq, 1.8 g, 13.0 mmole), dicyclohexylcarbadiimide (2 eq, 2.7 g, 13.0 mmole) and 4-dimethylaminpyridine (1 eq, 2.7 ml, 19.5 mmole), prepared under an argon atmosphere, at room temperature under argon. The resulting suspension is stirred at room temperature for 20 hours under argon, then diluted with 300 ml of methylene chloride. The methylene chloride extracts are washed thoroughly with saturated aqueous sodium bicarbonate solution and water, dried over anhydrous magnesium sulfate, filtered and concentrated. The residue is chromatographed through a silica gel (200 g) flash column and eluted by ether to give 1.48 g (72.2%) of N,N-dimethylamino acetic acid, 2,3-diethyl-4-methoxynaphth-1-yl ester as a yellowish brown oil.

Physical characteristics are as follows:
Mass spectra (m/e): 315, 287, 229, and 58.
IR (cm$^{-1}$): 1775, 1595, 1452, 1358, and 1131.
$^1$H-NMR ($\delta$, $CDCl_3$): 8.20–7.90, 7.65–7.30, 3.93, 3.67, 3.00–2.50, 2.53, 1.24 and 1.19.
Anal. Calc'd. for $C_{19}H_{25}NO_3$: 315.1834. Found: 315.1845.

EXAMPLE 16

L-Valine, 2-n-butyl-4-methoxynaphth-1-yl ester and its hydrochloric acid salt (Formula I: D is —CH=CH—, $R_3$ is —C(O)AA, —C(O)AA is the acyl portion of L-valine, $R_2$ is butyl, $R_1$ is hydrogen)

Part A

Dry methylene chloride (20 ml) is added to a mixture of 2-n-butyl-4-methoxynaphthol (1.0 g, 4.35 mmole), t-Boc-L-valine (1.1 eq, 1.04 g), dicyclohexylcarbodiimide (1.1 eq, 0.985 g), prepared under an argon atmosphere, at 0° C. (ice bath). The ice bath is removed and the resulting solution is stirred at room temperature for 18 hours under argon. The white precipitate is removed by filtration through the celite, which is washed with 200 ml of ether. The filtrate is washed twice with 50 ml of brine, dried over anhydrous sodium sulfate, filtered and concentrated. The yellow residue is chromatographed through a silica gel flash column and eluted by 10% ether in n-hexane, to give 1.29 g (69.0%) of t-Boc-L-valine, 2-n-butyl-4-methoxynaphth-1-yl ester as a pale yellow syrup.

Physical characteristics are as follows:
Mass spectra (m/e): 356, 286, 230, and 1.87.
IR (cm$^{-1}$): 1760, 1718, 1635, 1601, 1509, and 1462.
$^1$H-NMR ($\delta$, $CDCl_3$): 8.30–8.10, 7.75–7.35, 6.64, 5.00, 4.75–4.55, 3.98, 2.70–2.45, 1.48, 1.70–1.40, and 1.30–0.90.

Part B

Trifluoroacetic acid (25 ml) is added to a cooled (ice bath) solution of the t-Boc-L-valine, 2-n-butyl-4-methoxynaphth-1-yl ester (1.24 g, 2.89 mmole) in dry methylene chloride (50 ml), prepared under an argon atmosphere. The ice bath is removed, and the resulting solution is stirred at room temperature for 1 hour under argon. The solvents are removed using a rotary evaporator, and the residue is dissolved in 150 ml of methylene chloride. The methylene chloride extracts are washed with 75 ml of water, saturated aqueous sodium bicarbonate solution (75 ml), then twice with 75 ml of water, dried over anhydrous sodium sulfate, filtered and concentrated. The residue is chromatographed through a silica gel flash column and eluted by 0.3% methanol in methylene chloride to give 0.94 g (99.0%) of L-Valine, 2-n-butyl-4-methoxynaphth-1-yl ester as a white solid.

Physical characteristics are as follows:
Mass spectra (m/e): 329, 230, 187, 173, and 72.
IR (cm$^{-1}$): 3411, 1751, 1466, 1379, 1224, and 1137.
$^1$H-NMR ($\delta$, $CDCl_3$): 8.35–8.10, 7.75–7.30, 6.65, 3.99, 3.76, 2.70–2.35, 1.70–1.40, and 1.35–0.90.

The free amine is treated with hydrochloric acid gas in anhydrous ether, and the resulting hydrochloric acid salt is recrystallized from methylene chloride and n-hexane in accordance with the procedure of Example 13, Part B.

Physical characteristics are as follows:
Melting point: 205°–209° C.
Mass spectra (m/e): 329, 230, 215, 187, and 72.
IR (cm$^{-1}$): 1756, 1635, 1463, 1377, and 1213.
Anal. Calc'd. for $C_{20}H_{28}NO_3Cl$: C, 65.65; H, 7.71; N, 3.83; Cl, 9.69. Found: C, 66.01; H, 7.99; N, 3.68; Cl, 9.45.

EXAMPLE 17

L-Alanine, 2-n-butyl-4-methoxynaphth-1-yl ester and its hydrochloric acid salt (Formula I: D is —CH=CH—, $R_3$ is —C(O)AA, —C(O)AA is the acyl portion of L-alanine, $R_2$ is butyl, $R_1$ is hydrogen)

Part A

Dry methylene chloride (30 ml) is added to a mixture of 2-n-butyl-4-methoxynaphthol (1.697 g, 7.37 mmole), t-Boc-L-Alanine (1.1 eq, 1.56 g), dicyclohexylcarbodiimide (1.1 eq, 1.68 g) and 4-dimethylaminpyridine (0.1 eq, 93 mg) under an argon atmosphere at 0° C. (ice bath). The ice bath is removed, and the resulting solution is stirred at room temperature for 18 hours under argon. The white precipitate is removed through the celite, which is washed with 200 ml of methylene chloride. The combined filtrates are washed three times with water, dried over magnesium sulfate, filtered and concentrated. The residue is chromatographed through a silica gel flash column and eluted by 20–35% ether in n-hexane, to give 2.51 g (84.8%) of t-Boc-L-Alanine, 2-n-butyl-4-methoxynaphth-1-yl ester as a colorless syrup.

Physical characteristics are as follows:
Mass spectra (m/e): 230, 187, and 57.
IR ($cm^{-1}$): 3474, 1751, 1679, 1518, 1375, and 1298.
$^1$H-NMR ($\delta$, $CDCl_3$): 8.25–8.15, 7.75–7.30, 6.64, 5.20–5.00, 4.85–4.55, 3.99, 2.75–2.40, 1.70, 1.48, and 1.10–0.85.
Anal. Calc'd. for $C_{23}H_{31}NO_5$: C, 68.80; H, 7.78; N, 3.47. Found: C, 68.95; H, 7.97; N, 3.42.

Part B

Trifluoroacetic acid (25 ml) is introduced under an argon atmosphere to a cooled (ice bath) solution of the t-Boc-L-Alanine, 2-n-butyl-4-methoxynaphth-1-yl ester (2.5 g, 6.23 mmole) in dry methylene chloride (25 ml). The ice bath is removed and the resulting solution is stirred at room temperature for 1 hour under argon, and the solvents are removed using a rotary evaporator and the residue is dissolved in methylene chloride. The methylene chloride extracts are washed once with water, once with saturated aqueous sodium bicarbonate solution, and twice with water, dried over anhydrous sodium sulfate, filtered and concentrated. The residue is chromatographed through a silica gel (225 g) flash column and eluted by 30% ethyl acetate in methylene chloride, to give 1.64 g (87.3%) of L-Alanine, 2-n-butyl-4-methoxynaphth-1-yl ester as a colorless oil.

Physical characteristics are as follows:
Mass spectra (m/e): 301, 230, and 187.
IR ($cm^{-1}$): 3380, 1756, 1601, 1461, 1376, 1221, and 1161.
$^1$H-NMR ($\delta$, $CDCl_3$): 8.35–8.10, 7.75–7.30, 6.64, 3.99, 4.15–3.90, 2.75–2.45, 1.67, 1.90–1.20, and 1.10–0.80.
Anal. Calc'd. for $C_{18}H_{23}NO_3$: 301.1678. Found: 301.1682.

In accordance with the procedure of Example 13, Part B, the alanine ester is converted to the hydrochloric acid salt, and recrystallized from methanol and ether.

Physical characteristics are as follows:
Melting point: 185°–187° C.
Mass spectra (m/e): 301, 230, 215, and 187.
IR ($cm^{-1}$): 1765, 1638, 1504, 1460, 1376, and 1188.
Anal. Calc'd. for $C_{18}H_{24}NClO_3$: C, 63.99; H, 7.16; N, 4.15; Cl, 10.49. Found: C, 63.89; H, 7.38; N, 4.05; Cl, 9.85.

EXAMPLE 18

L-Phenylalanine, 2-n-butyl-4-methoxynaphth-1-yl ester and its hydrochloric acid salt (Formula I: D is CH=CH—, $R_3$ is —C(O)AA, —(O)AA is the acyl portion of L-phenylalanine, $R_2$ is butyl, $R_1$ is hydrogen)

Part A

Dry methylene chloride (30 ml) is added to a mixture of 2-n-butyl-4-methoxynaphthol (1.0 g, 4.3 mmole), t-Boc-L-phenylalanine (1.5 eq, 1.7 g, 6.4 mmole), dicyclohexylcarbodiimide (1.5 eq, 1.4 g, 6.4 mmole) and 4-dimethylaminpyridine (0.74 eq, 0.04 g, 3.2 mmole), under an argon atmosphere at room temperature. The resulting solution is stirred at room temperature for 20 hours under argon. After the white precipitates are removed by filtration, the filtrate is washed twice with 100 ml of saturated aqueous sodium bicarbonate solution, three times with 100 ml of water, dried over anhydrous sodium sulfate, filtered and concentrated. The residue is chromatographed through a silica gel (200 g) flash column and eluted by 10–15% ether in n-hexane to give 1.78 g (86.8%) of t-Boc-L-phenylalanine, 2-n-butyl-4-methoxynaphth-1-yl ester as a white amorphous crystal.

Physical characteristics are as follows:
Mass spectra (m/e): 404, 230, and 187.
IR ($cm^{-1}$): 3344, 1770, 1695, 1535, 1463, and 1156.
$^1$H-NMR ($\delta$, $CDCl_3$): 8.25–8.00, 7.50–7.20, 6.63, 5.20–4.90, 3.98, 3.60–3.20, 2.60–2.40, 1.43, 1.60–1.30, and 1.05–0.85.
Anal. Calc'd. for $C_{29}H_{35}NO_5$: C, 72.93; H, 7.39; N, 2.93. Found: C, 72.88; H, 7.65; N, 2.83.

Part B

The cooled (ice bath) solution of the t-Boc-L-Phenylanine, 2-n-butyl-4-methoxynaphth-1-yl ester (1.68 g, 3.5 mmole) in dry methylene chloride (40 ml), prepared under argon atomsphere, is treated with trifluoroacetic acid (10 ml). The resulting yellow solution is stirred at 0° C. for 30 minutes under argon. The ice bath is removed, and the reaction solution is stirred at room temperature for an additional 45 minutes under argon. The solvents are removed using a rotary evaporator, and the residue is dissolved in 300 ml of methylene chloride. The methylene chloride extracts are washed three times with 200 ml of water, dried over anhydrous sodium sulfate, filtered and concentrated. The residue is chromatographed through a silica gel (200 g) flash column and eluted by 1% methanol in methylene chloride, to give 1.3 g (98.5%) of L-phenylalanine, 2-n-butyl-4-methoxynaphth-1-yl ester as a pale yellow oil.

Physical characteristics are as follows:
Mass spectra (m/e): 230, 214, 120, and 91.
IR ($cm^{-1}$): 3380, 3320, 3060, 3030, 3000, 2960, 2940, 2860, 1755, 1635, 2600, 1585, 1510, 1495, 1460, 1375, 1220, 700, 750, and 700.
$^1$H-NMR ($\delta$, $CDCl_3$): 8.30–8.15, 7.65–7.25, 6.64, 4.30–4.00, 3.99, 3.60–2.90, 2.65–2.40, 1.70–1.20, and 1.00–0.75.

In accordance with the precedure of Example 13, Part B, the free amine is converted to the hydrochloric acid salt, and recrystallized from absolute ethanol and ether in n-hexane.

Physical characteristics are as follows:

Melting point: 225°–227° C.
Mass spectra (m/e): 377, 349, 230, 187, and 120.
IR (cm$^{-1}$): 3060, 2800, 2720, 2660, 2650, 2060, 1760, 1635, 1600, 1525, 1220, 1190, 1165, 1120, 770, 755, 730, and 700.
Anal. Calc'd. for $C_{24}H_{28}ClNO_3$: C, 69.64; H, 6.82; N, 3.38; Cl, 8.57. Found: C, 69.39; H, 6.91; N, 3.46; Cl, 8.64.

EXAMPLE 19

Following the procedure of the preceding Examples, and those depicted in Chart A, all of the compounds of this invention are prepared.

EXAMPLE 20

Treatment of deep vein thrombosis using 2,3-diethyl-4-methoxy-1-naphthalenol, acetate Nine adult domestic short hair cats weighing 4.5–5 kg were anesthetized with sodium pentabarbital (25–30 mg/kg i.v.). The neck area was prepared for a sterile cut down procedure and the jugular veins were exposed. After exposure of the veins each animal was injected with epsilon amino caproic acid (eaca) to inhibit plasminogen activation (2.5 grams i.v. in Tyrode's solution). This was done to reduce the normally highly active feline fibrinolytic mechanism and, thus reduce lysis of fibrin thrombi which might form in the vessel. Six of the cats were also treated with 2,3-diethyl-4-methoxy-1-naphthalenol, acetate. Three of the cats were given 1 mg/kg i.v. and 3 of the cats were treated with 5 mg/kg i.v. prior to venous occlusion. The jugular veins were carefully dissected free of surrounding connective tissue and the vein was ligated at the thoracic inlet with 3-0 dexon. The skin incision was closed and the animals were maintained in surgical anesthesia for 2 hours. At the end of the 2 hour waiting period, the jugular veins were exposed again. A 25 gauge butterfly needle was positioned into the lumen and blood was flushed out of the vein with heparinized Tyrode's solution (1U heparin/ml). The veins were tied off and removed under physiologic pressure. The vessels were immediately immersed in a 2.5% glutaraldehyde solution prepared in Tyrode's solution for fixation. The veins were fixed overnight at 5 degrees centigrade, postfixed in 1% osmium tetroxide overnight, dehydrated in ethanol and substituted by amyl acetate. All veins were critical point dried from carbon dioxide using a Denton DCP-1 critical point drying apparatus. The veins were mounted on stubas, gold coated on a Denton DV-502 modified vacuum evaporator and examined on a Cambridge Stereoscan 150 scanning electron microscope.

Two hours of jugular vein stasis following the trauma of dissection caused massive white cell adhesion to and migration under the venous endothelium of non-treated cats and produced sloughing of the endothelium and exposure of the basement membrane. This damage was sufficient to initiate thrombosis. Many of the exposed areas of basement membrane had adherent platelets. The platelets were adherent as monolayers or as aggregates. In some areas fibrin was found deposited on the endothelium or exposed basement membrane. Leukocytes were occasionally associated with the fibrin.

2,3-Diethyl-4-methoxy-1-naphthylenol, acetate had a dose dependent effect on the vascular changes described above. The 1 mg/kg dose did not reduce leukocyte adhesion or migration. Most of the surface of all the veins examined in this group had multiple aggregates of leukocytes visible under the intact endothelium. Although leukocyte migration was not inhibited, leukocyte release of hydrolytic enzymes and production of superoxide's was apparently inhibited. Few areas with detached endothelial cells or exposed basement membrane was found in this group.

The 5 mg/kg dose had an even greater inhibitory effect on leukocyte mediated damage. In this group only patchy areas of adherent leukocytes were observed. In most of these areas leukocytes were also found under the endothelium. It was only in these areas, however, that endothelial cell loss and platelet deposition was observed. The numbers of adhering and migrating leukocytes found in this group appeared to be less than in either the control of 1 mg/kg treated group. With the exception of one vein, approximately half or more of the vascular surface had an intract endothelial cell cover with few adherent leukocytes. Only occasional small areas of fibrin deposition were found in this group.

EXAMPLE 21

Treatment of mucous secretion using 2-butyl-4-methoxy-1-naphthalenol, acetate.

Mongrel dogs (weight 18–35 kg) were anesthetized with a mixture of chloralose (100 mg/kg) and urethane (500 mg/kg) via intravenous injection. The animals were secured to a surgery table, ventral side up, and the neck and inner right hind limb were shaved. A ventral midline incision was made in the neck using a Bovie CSVII electrosurgical unit, starting from the papillae (interramal) to the clavicle thus exposing the trachea. An endotracheal tube was secured into the lower trachea. The animals were then connected via the endotracheal tube to a Harvard respirator (Model 607A) that delivered room air at a constant tidal volume and frequency. Two polyethylene catheters were connected to the endotracheal tube, and one was connected to a medical gas analyzer (Beckman, Model LB-2) that continuously measured the carbon dioxide ($CO_2$) content of the expired air for determination of end tidal $CO_2$. The other was connected to a pressure transducer (Statham, Model PMI 131TC+2.5-350) for the measurement of airway press ure.

A second incision made in the inner right hind limb to expose the femoral artery and vein was made for the catheterization of these large vessels. A polyethylene catheter was tied into the artery and connected to a pressure transducer (Statham, Model P231D) for the measurement of blood pressure. This catheter also allowed for samples of arterial blood to be collected for measurements of blood gas tension using a blood gas analyser (Corning, Model 175). Another polyethylene catheter was tied into the femoral vein which was used for injecting additional anesthetic and paralyzing drugs. Gallamine triethiodide (20–40 mg) was used to paralyze the respiratory muscles and a single injection of sodium bicarbonate 7.5% (0.5 mg/kg) in conjunction with a continuous i.v. drip of 5% dextrose in 0.9% saline helped to maintain fluid balance. All physiological measurements were recorded and monitored on a polygraph (Grass instruments, Model 7D). Once the femoral cutdown was completed, surgery on the neck region resumed. The carotid artery was exposed and the "knuckle" (a portion of the carotid which bisects to supply blood flow to the trachea and neck muscles) was located. A small polyethylene catheter was then inserted into the muscular branch of the cranial thyroid artery (CTA). This allowed for close arterial injection of experimental agents. The strap muscles were removed and the mucosal surface of the trachea exposed by cutting along the anterior midline of the upper two-thirds of the extrathoracic trachea and pulling the cut edges widely apart. The exposed mucosa was checked for proper canulation by blanching and appropriate adjustments of the canula into the CTA were made until blanching was achieved.

Isometric tension measurements of the trachealis muscle were recorded by suturing a rigid, plastic bar to the (15) cartilaginous rings of the cut edges of the trachea, and connecting one side to a fixed restraint and the contralateral side to a force displacement transducer (Grass, Model FT 03C). An initial tension of 25-30 g/cm of trachea was applied to the muscle, and it was allowed to stabilize for 45 min. An initial zero tension point was determined before agonists were injected into the CTA, and the zero was readjusted after agonist injections.

To visualize secretions coming from the submucosal gland duct openings of the trachea, powdered tantalum, an inert metal (2-5 microns in size) was sprayed on the trachea until it formed a uniform layer over the mucosal surface. The tantalum itself did nothing to normal secretion, but prevented the normal ciliary dispersion of secretions from the gland duct openings; these secretions, therefore, caused elevations ("hillocks") in the tantalum layer. The number of hillocks formed in a 1.2 $cm^2$ field, 1-2 cm from the larynx, were counted and their images were recorded with a video camera (Hitachi CCTV, Model HV-17TU) mounted on a dissecting microscope (Zeiss Ompi-1) with a beam splitter. Only those hillocks over 0.1 mm in diameter were counted. The camera was connected to a videotape recorder (Sony, Model VO-2610) and a time signal generator (Panasonic WJ-810). The appearance of hillocks and the time signal were recorded simultaneously on a videotape. The images were displayed on a television monitor (Sony Trinitron KV 1914), and the hillocks were manually counted for 1-4 minutes. The formed secretions were then removed by gently wiping the mucosa with small pieces of tissue paper soaked in saline (0.9%).

Two stimulators of mucous secretion utilized in these studies of mucous secretion were (1) hypoxia and (2) arachidonic acid (AA). Hypoxia causes the trachealis muscle to contract and mucous production to increase by stimulation of the carotid body chemoreceptor. To achieve a hypoxic condition in the animals, a mixture of 8% oxygen ($O_2$) and 92% nitrogen ($N_2$) was forced into a 8 cu ft weather balloon which was connected in-line with the Harvard respirator. An adjustable clamp facilitated in changing from room air to hypoxic air breathed directly by the dog via the Harvard respirator. Hillocks were counted for 2 to 3 minutes with the dog on hypoxia after the animal was exposed to hypoxia for at least 30 seconds. A quick adjustment of the clamp allowed the animals to breath room air again, and all physiological parameters altered with hypoxia returned to "normal" within a few minutes.

When drug activity was assessed with arachidonic acid induced secretion, the animals were pretreated with indomethacin (Indo) (5 mg/kg) for at least 30 minutes. Before any drugs were given, however, the appropriate controls for arachidonate and indomethacin were run. The standard procedure for this was to determine the effect of (1) arachidonate alone, (2) indomethacin alone, and (3) indomethacin/arachidonate combination on normal baseline secretion. Once these control values were acquired, the drug was given. An experimental drug given in the presence of the indomethacin/arachidonate combination helps to characterize that portion of the response due to lipoxygenase products. The dose of arachidonate was 1.0 mg in the CTA which stimulates mucus secretion and causes a slight stimulation followed by relaxation of the trachealis muscle. The indomethacin blocked about 20% of normal baseline secretion and nicely blocked the effect of arachidonate alone. Hillocks were counted for 2-3 minutes immediately after the arachidonate was given.

Experimental drugs were given via the CTA and/or by aerosol. When administered into the CTA, the dose was 1 mg/segment (unless a dose response was run). When drug was administered by aerosol, the animal was connected to a Mark VII Bird Respirator by the endotracheal tube.

By connecting the Mark VII to the inhalation port adjoined to the endotracheal tube, the Harvard pump automatically triggered the Bird Respirator to generate an aerosol mist as the dog inhaled, thus forcing the mist into the animal's lungs. The animals were allowed to breathe 15 breaths of a 1% solution or dilutions of drug and the hillocks were counted four minutes after drug administration.

Inhibition or stimulation of mucous secretion was determined by the following comparisons: Drug alone to baseline; drug+hypoxia to hypoxia alone; and drug+indomethacin+AA to indomethacin/AA alone. The results are summarized in Table I.

TABLE I

Hillock Canine Mucus Summary Data

| Dose of Drug | Route | n | Baseline | Hypoxia | Indo/AA |
|---|---|---|---|---|---|
| 0.001% | Inhalation | 4 | 24 † | 87* | 100** |
| 0.01 | | 5 | 19 | 91 | 100** |
| 0.1 | | 4 | 23 | 96* | 100** |
| 1.0 | | 6 | 6 | 100*** | 100*** |
| | Predose Time (hr) | | | | |
| 10 mg/kg Oral | 3 | 2 | 5 † | 94 | 100* |
| | 4 | 2 | ND | ND | 100* |
| | 5 | 2 | ND | ND | 100* |
| 5 mg/kg Oral | 3.5 | 2 | 30 † | 49 | 69 |
| | 4.5 | 2 | ND | ND | 95 |
| 1.0 mg/kg Oral | 3.5 | 2 | 6 † | 11 † | 50 |
| | 5.0 | 2 | | | 62* | n: Represents the number of animals tested.
p Value = Mean exceeds zero by a statistically significant amount based on a one-way or two-way analysis of variance.
*p <0.05;
**p <0.005;
***p <0.0001.
† Indicates stimulation.
ND: Represents "not done."

We claim:
1. A compound of the Formula I

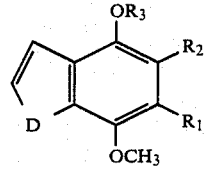

wherein $R_1$ and $R_2$ are the same or different and are
(a) hydrogen, (b) $(C_1-C_{10})$alkyl,
(c) $(C_2-C_{10})$alkenyl, or
(d) PhX;

wherein (PhX) is phenyl substituted by zero to 3 of the following:
(a) $(C_1-C_4)$alkyl,
(b) chloro,
(c) fluoro,
(d) bromo,
(e) nitro,
(f) trifluoromethyl; or
(g) $OR_4$;

wherein D is
(a) —CH=CH—,
(b) =N(CH$_3$),
(c) —S—,
(d) —O—;

wherein $R_3$ is
(a) CH$_3$—C(O)—,
(b) hydrogen;
(c) —C(O)—(CR$_{17}$R$_{18}$)$_m$—(CH$_2$)$_n$—NR$_{14}$R$_{15}$,
(d) —C(O)—AA, or
(e) —C(O)—PhX—NH$_2$;

wherein m is 1, 2, 3, or 4;
wherein n is 0, 1, 2, 3, 4, or 5;
wherein —C(O)AA is the acyl portion derived from any naturally occurring alpha-amino acid;
wherein $R_{14}$ and $R_{15}$ are the same or different and are:
(a) hydrogen,
(b) $(C_1-C_{10})$alkyl,
(c) —C(O)R$_{16}$,
(d) —C(O)—PhX, or
(e) —PhX;

with the proviso that $R_{14}$ and $R_{15}$ are other than hydrogen when n is zero;
wherein $R_{16}$ is $(C_1-C_4)$alkyl;
wherein $R_{17}$ and $R_{18}$ are the same or different and are:
(a) hydrogen,
(b) $(C_1-C_{10})$alkyl,
(c) —CH$_2$—PhX, or
(d) —PhX;

with the proviso that each occurrence of $R_{17}$ and $R_{18}$ may be the same or different; wherein PhX—NH$_2$ is an amino-substituted phenyl group additionally substituted by zero to 3 of the following:
(a) $(C_1-C_4)$alkyl,
(b) chloro,
(c) fluoro,
(d) bromo,
(e) nitro,
(f) trifluoromethyl, or
(g) $OR_4$;

wherein $R_4$ is
(a) hydrogen, or
(b) $(C_1-C_4)$alkyl;

with the following provisos
(1) when D is —CH=CH— or =N(CH$_3$), $R_3$ is not hydrogen;
(2) when D is —CH=CH— and one of $R_2$ and $R_1$ is hydrogen or methyl, the other is not hydrogen or methyl;
(3) when D is =N(CH$_3$), $R_1$ and $R_2$ are not phenyl; and
(4) when D is —CH=CH— and $R_2$ is phenyl, $R_1$ is other than hydrogen;

or a pharmacologically acceptable acid addition salt thereof, when $R_3$ is
(c) —C(O)—(CR$_{17}$R$_{18}$)$_m$—(CH$_2$)$_n$—NR$_{14}$R$_{15}$,
(d) —C(O)—AA, or
(e) —C(O)—PhX—NH$_2$.

2. A compound of claim 1, wherein $R_2$ is n-butyl and $R_1$ is hydrogen or $R_1$ and $R_2$ are both ethyl.

3. A compound of claim 2, wherein D is —CH=CH—.

4. A compound of claim 1, 4-Methoxy-2,3-diphenyl-1-naphthalenol, acetate.

5. A compound of claim 1, 7-Methoxy-1methyl-5,6-diphenyl-1H-indol-4-ol, acetate (ester).

6. A compound of claim 2 5-Butyl-7-methoxy-4-benzofuranol.

7. A compound of claim 2 5-Butyl-7-methoxy-benzo(b)thiophen-4-ol.

8. A compound of claim 2 5-Butyl-7-methoxy-1-methyl-1H-indol-4-ol, acetate (ester).

9. A compound of claim 2 5,6-Diethyl-7-methoxy-1-methyl-1H-indol-4-ol, acetate (ester).

10. A compound of claim 2 5-Butyl-7-methoxy-4-benzofuranol, acetate.

11. A compound of claim 2 5-Butyl-7-methoxy-benzo(b)-thiophen-4-ol, acetate.

12. A compound of claim 3 2-Butyl-4-methoxy-1-naphthalenol, acetate.

13. A compound of claim 3 2,3-Diethyl-4-methoxy-1-naphthalenol, acetate.

14. A compound of claim 3, wherein $R_3$ is
(a) —C(O)—(C$_{R17}$R$_{18}$)$_m$—(CH$_2$)$_n$—NR$_{14}$R$_{15}$,
(b) —C(O)—AA, or
(c) —C(O)—PhX—NH$_2$.

15. A compound of claim 14, selected from the group consisting of:
(a) L-Valine, 2,3-diethyl-4-methoxynaphth-1-yl ester,
(b) L-Valine, 2,3-diethyl-4-methoxynaphth-1-yl ester, hydrochloride,
(c) L-Alanine, 2,3-diethyl-4-methoxynaphth-1-yl ester,
(d) L-Phenylalanine, 2,3-diethyl-4-methoxynaphth-1-yl ester, hydrochloride,
(e) 3-(N,N-Diethylamino)propionic acid, 2,3-diethyl-4-methoxynaphth-1-yl ester,
(f) N,N-Dimethylamino acetic acid, 2,3-diethyl-4-methoxynaphth-1-yl ester,
(g) L-Valine, 2-n-butyl-4-methoxynaphth-1-yl ester,
(h) L-Valine, 2-n-butyl-4-methoxynaphth-1-yl ester, hydrochloride,
(i) L-Alanine, 2-n-butyl-4-methoxynaphth-1-yl ester, and
(j) L-Phenylalanine, 2-n-butyl-4-methoxynaphth-1-yl ester, hydrochloride.

16. A compound of claim 15 L-Valine, 2,3-diethyl-4methoxynaphth-1-yl ester hydrochloride.

17. A compound of claim 15 L-Valine, 2-n-butyl-4-methoxynaphth-1-yl ester.

18. A compound of claim 15 L-Valine, 2-n-butyl-4-methoxynaphth-1-yl ester hydrochloride.

19. A compound of claim 15 L-Alanine, 2-n-butyl-4-methoxynaphth-1-yl ester.

20. A method for reducing or preventing the hypersecretion of mucus in the respiratory tract of a patient in need thereof which comprises: administering to said patient an effective amount of the compound of Formula I,

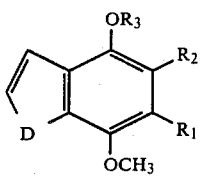

wherein $R_1$ and $R_2$ are the same or different and are
(a) hydrogen,
(b) $(C_1-C_{10})$alkyl,
(c) $(C_2-C_{10})$alkenyl, or
(d) PhX;
wherein (PhX) is phenyl substituted by zero to 3 of the following:
(a) $(C_1-C_4)$alkyl,
(b) chloro,
(c) fluoro,
(d) bromo,
(e) nitro,
(f) trifluoromethyl; or
(g) $OR_4$;
wherein D is
(a) —CH=CH—,
(b) =N(CH$_3$),
(c) —S—,
(d) —O—;
wherein $R_3$ is
(a) CH$_3$—C(O)—,
(b) hydrogen;
(c) —C(O)—(CR$_{17}$R$_{18}$)$_m$—(CH$_2$)$_n$NR$_{14}$R$_{15}$,
(d) —C(O)—AA, or
(e) —C(O)—PhX—NH$_2$;
wherein m is 1, 2, 3, or 4;
wherein n is 0, 1, 2, 3, 4, or 5;
wherein —C(O)AA is the acyl portion derived from any naturally occurring alpha-amino acid,
wherein $R_{14}$ and $R_{15}$ are the same or different and are:
(a) hydrogen,
(b) $(C_1-C_{10})$alkyl,
(c) —C(O)R$_{16}$,
(d) —C(O)—PhX, or
(e) —PhX;
with the proviso that $R_{14}$ and $R_{15}$ are other than hydrogen when n is zero;
wherein $R_{16}$ is $(C_1-C_4)$alkyl;
wherein $R_{17}$ and $R_{18}$ are the same or different and are:
(a) hydrogen,
(b) $(C_1-C_{10})$alkyl,
(c) —CH$_2$—PhX, or
(d) —PhX;
with the proviso that each occurrence of $R_{17}$ and $R_{18}$ may be the same or different; wherein PhX—NH$_2$ is an amino-substituted phenyl group additionally substituted by zero to 3 of the following:
(a) $(C_1-C_4)$alkyl,
(b) chloro,
(c) fluoro,
(d) bromo,
(e) nitro,
(f) trifluoromethyl, or
(g) $OR_4$;
wherein $R_4$ is
(a) hydrogen, or
(b) $(C_1-C_4)$alkyl;
with the following provisos
(1) when D is —CH=CH— or =N(CH$_3$), $R_3$ is not hydrogen;
(2) when D is —CH=CH— and one of $R_2$ and $R_1$ is hydrogen or methyl, the other is not hydrogen or methyl;
(3) when D is =N(CH$_3$), $R_1$ and $R_2$ are not phenyl; and
(4) when D is —CH=CH— and $R_2$ is phenyl, $R_1$ is other than hydrogen;
or a pharmacologically acceptable acid addition salt thereof, when $R_3$ is
(c) —C(O)—(CR$_{17}$R$_{18}$)$_m$—(CH$_2$)$_n$—NR$_{14}$R$_{15}$,
(d) —C(O)—AA, or
(e) —C(O)—PhX—NH$_2$.

21. The method of claim 20 wherein $R_1$ and $R_2$ are the same or different and are hydrogen or $(C_1-C_{10})$alkyl.

22. The method of claim 21 wherein D is —CH=CH—.

23. The method of claim 22 wherein the compound is:
(a) 2-Butyl-4-methoxy-1-naphthalenol, acetate; or
(b) 2,3-Diethyl-4methoxy-1-naphthalenol, acetate.

24. The method of claim 22 wherein $R_3$ is:
(a) —C(O)—(CR$_{17}$R$_{18}$)$_m$—(CH$_2$)$_n$—NR$_{14}$R$_{15}$,
(b) —C(O)—AA, or
(c) —C(O)—PhX—NH$_2$.

25. The method of claim 24 wherein the compound is L-Valine, 2-n-butyl-4-methoxynaphth-1-yl ester, hydrochloride.

* * * * *

UNITED STATES PATENT OFFICE
CERTIFICATE OF CORRECTION

Patent No. 4,737,519          Dated 12 April 1988

Inventor(s) A. Yamashita et al.

It is certified that error appears in the above-identified patent and that said Letters Patent are hereby corrected as shown below:

Column 1, line 52: "Widdicobe" should read --Widdicombe--.
Column 3, line 14: "Gonclalves" should read --Goncalves--.
Column 8, line 20: "covenient" should read --convenient--.
Column 9, line 28: "platlet" should read --platelet--.
Column 17, line 60: "[2-methyl" should read --[2-N-methyl
Column 18, line 21: "cm-1" should read --$cm^{-1}$--.
Column 19, line 1: "Recrystalization" should read --Recrystallization--.
Column 20, line 20: "litle" should read --title--.
Column 20, line 28: "$HH_{21}$" should read --$H_{21}$--.

Column 20, line 46: "chromagraphed" should read --chromatographed--.
Column 25, line 52: "carbadiimide" should read --carbodiimide--.
Column 28, line 64: "precedure" should read --procedure--.
Column 34, line 10: "-lmethyl" should read -- -1-methyl--.
Column 34, line 12: "claim 2 5-" should read --claim 2, 5- --.
Column 34, line 14: "claim 2 5-" should read --claim 2, 5- --.
Column 34, line 16: "claim 2 5-" should read --claim 2, 5- --.
Column 34, line 18: "claim 2 5," should read --claim 2, 5,--.
Column 34, line 20: "claim 2 5-" should read --claim 2, 5- --.
Column 34, line 22: "claim 2 5-" should read --claim 2, 5- --.
Column 34, line 25: "claim 3 2-" should read --claim 3, 2- --.

UNITED STATES PATENT OFFICE
CERTIFICATE OF CORRECTION

Patent No. 4,737,519                    Dated 12 April 1988

Inventor(s) A. Yamashita et al.

It is certified that error appears in the above-identified patent and that said Letters Patent are hereby corrected as shown below:

Column 34, line 27: "claim 3 2," should read --claim 3, 2,--.
Column 34, line 55: "claim 15 L-" should read --claim 15, L- --.
Column 34, line 56: "4methoxy" should read --4-methoxy--.
Column 34, line 59: "claim 15 L-" should read --claim 15, L- --.
Column 34, line 59: "claim 15 L-" should read --claim 15, L- --.
Column 34, line 61: "claim 15 L-" should read --claim 15, L- --.

Signed and Sealed this

Twenty-second Day of November, 1988

*Attest:*

DONALD J. QUIGG

*Attesting Officer*      *Commissioner of Patents and Trademarks*